(12) United States Patent
Toth et al.

(10) Patent No.: US 11,414,446 B1
(45) Date of Patent: Aug. 16, 2022

(54) COMPOUNDS AND THE USE THEREOF IN METATHESIS REACTIONS

(71) Applicant: Verbio Vereinigte Bioenergie AG, Zörbig (DE)

(72) Inventors: Florian Toth, Budapest (HU); Georg Frater, Horw (CH); Levente Ondi, Budapest (HU)

(73) Assignee: Verbio Vereinigte Bioenergie AG

( * ) Notice: Subject to any disclaimer, the term of this patent is extended or adjusted under 35 U.S.C. 154(b) by 0 days.

(21) Appl. No.: 16/988,199

(22) Filed: Aug. 7, 2020

Related U.S. Application Data

(63) Continuation of application No. 16/167,250, filed on Oct. 22, 2018, now abandoned, which is a continuation of application No. 15/303,089, filed as application No. PCT/IB2015/000473 on Apr. 9, 2015, now Pat. No. 10,106,566.

(60) Provisional application No. 62/007,987, filed on Jun. 5, 2014.

(30) Foreign Application Priority Data

Apr. 11, 2014 (GB) .................................. 1406591

(51) Int. Cl.
| | | |
|---|---|---|
| C07F 11/00 | (2006.01) | |
| B01J 31/12 | (2006.01) | |
| B01J 31/22 | (2006.01) | |
| C07C 67/475 | (2006.01) | |
| C07D 321/00 | (2006.01) | |
| C07C 67/333 | (2006.01) | |
| C07C 6/04 | (2006.01) | |

(52) U.S. Cl.
CPC ........... *C07F 11/00* (2013.01); *B01J 31/2265* (2013.01); *C07C 6/04* (2013.01); *C07C 67/333* (2013.01); *C07C 67/475* (2013.01); *C07D 321/00* (2013.01); *B01J 2231/543* (2013.01); *B01J 2531/64* (2013.01); *B01J 2531/66* (2013.01); *C07C 2531/22* (2013.01); *C07C 2601/10* (2017.05)

(58) Field of Classification Search
CPC .................... C07F 11/00; B01J 31/12
USPC .............. 548/402; 556/58; 502/167
See application file for complete search history.

(56) References Cited

U.S. PATENT DOCUMENTS

| | | | |
|---|---|---|---|
| 6,121,473 | A | 9/2000 | Schrock et al. |
| 8,362,311 | B2 | 1/2013 | Schrock et al. |
| 9,776,179 | B2 * | 10/2017 | Wampler ................ C07C 45/41 |
| 10,106,566 | B2 | 10/2018 | Toth |
| 10,596,562 | B2 * | 3/2020 | Wampler ................ C07C 6/04 |
| 2008/0119678 | A1 | 5/2008 | Hock et al. |
| 2011/0007742 | A1 | 1/2011 | Leung et al. |
| 2011/0015430 | A1 | 1/2011 | Schrock et al. |
| 2011/0113679 | A1 | 5/2011 | Cohen et al. |
| 2014/0275595 | A1 | 9/2014 | Wampler et al. |
| 2014/0275681 | A1 | 9/2014 | Cohen et al. |
| 2019/0119311 | A1 | 4/2019 | Toth |

OTHER PUBLICATIONS

International Search Report and Written Opinion dated Sep. 21, 2015 for PCT/IB2015/000473.
Notice of Allowance dated Jun. 15, 2018 for U.S. Appl. No. 15/303,089.
Notice of Allowance dated Sep. 13, 2019 for U.S. Appl. No. 16/167,250.
Office Action dated Feb. 8, 2019 for U.S. Appl. No. 16/167,250.
Office Action dated Feb. 9, 2018 for U.S. Appl. No. 15/303,089.
Bartoszek, et al., A Convenient Protocol for the Synthesis of Axially Chiral Bronsted Acids, Tetrahedron 64 ,2008 ,1316-1322.
Gerber, et al., Molybdenum and Tungsten Monoalkoxide Pyrrolide (MAP) Alkylidene Complexes that Contain a 2,6-Diemsitylphenylimido Ligand, Organometallics, 32 ,2013 ,2373-2378.
Hock, et al., Dipyrrolyl Precursors to Bisalkoxide Molybdenum Olefin Metathesis Catalysts, J Am Chem Soc., 128(50) , 2006 ,16373-16375.
Hua, et al., Resolution of 8'-Alkoxy-1,1'-Binaphthalen-8-Ols, Asymmetry 12 ,2001 ,1999-2004.
Johnson, et al., Alkylidene Transfer from Phosphoranes to Tungsten(IV) Imido Complexes, Journal of the American Chemical Society, vol. 115 ,Jan. 1, 1993 ,8167-8177.
Kreickmann, et al., Imido Alkylidene Bispyrrolyl Complexes of Tungsten, Organometallics, 26 ,2007 ,5702-5711.
Marinescu, et al., Syntheses and Structures of Molybdenum Imido Alkylidene Pyrrolide and Indolide Complexes, Organometallics, 27 ,2008 ,6570-6578.

(Continued)

*Primary Examiner* — Charanjit Aulakh
(74) *Attorney, Agent, or Firm* — Dorsey & Whitney LLP

(57) ABSTRACT

The disclosure provides Group 6 complexes, which, in some embodiments, are useful for catalyzing olefin metathesis reactions. In some embodiments, the compounds are compounds of the following formula:

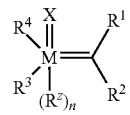

wherein:
M is a Group 6 metal atom;
X is an oxygen atom, $=N-R^5$, $=N-N(R^5)(R^{5'})$ or $=N-O-R^5$, $R^5$ and $R^{5'}$ independently being various substituents, such as aryl or heteroaryl, each optionally substituted;
n is 0 or 1;
$R^z$ is a neutral ligand;
$R^1$ is hydrogen or an organic substituent;
$R^2$ is an aryl or heteroaryl group, each optionally substituted;
$R^3$ is an anionic ligand; and
$R^4$ is an anionic ligand, such as a pyrrolide, a pyrazolide, an imidazolide, an indolide, an azaindolide, or an indazolide, each optionally substituted.

10 Claims, No Drawings

(56) References Cited

OTHER PUBLICATIONS

Satoh, et al., Palladium-Catalyzed Regioselective Mono- and Diarylation REactions of 2-Phenylphenols and Naphthols with Aryl Halides, Agnew. Chem. Int. Ed. Engl., 36, No. 16 ,1997.
Singh, et al., Milybdenum Imido Alkylidene Metathesis Catalysts that Contain Electron-Withdrawing Biphenolates or Binaphtholates, Organometallics, 26 ,2007 ,2528-2539.
Townsend, et al., High Oxidation State Molybdenum Imido Heteroatom-Substituted Alkylidene Compleses, Organometallics, vol. 32, No. 16 ,Aug. 26, 2013 ,4612-4617.
Wipf, et al., Enantioselective Synthesis of the AB-Ring System of the Antitumor Antibiotic Therazomine, J. Org. Chem., 66 , 2001 ,3133-3139.

\* cited by examiner

COMPOUNDS AND THE USE THEREOF IN METATHESIS REACTIONS

RELATED APPLICATIONS

This application is a continuation of U.S. patent application Ser. No. 16/167,250, filed Oct. 22, 2018, which is a continuation of U.S. patent application Ser. No. 15/303,089, filed Oct. 10, 2016, which is a National Stage Entry of International Application No. PCT/IB2015/000473, filed Apr. 9, 2015, which claims priority to U.S. Provisional Application No. 62/007,987, filed Jun. 5, 2014, and Great Britain Patent Application No. GB1406591.6, filed Apr. 11, 2014, each of which is incorporated herein by reference in its entirety.

TECHNICAL FIELD

Organometallic complexes and their use as catalyst compounds are generally disclosed herein. In some embodiments, the organometallic complexes disclosed herein catalyze a metathesis reaction between olefinically unsaturated compounds.

BACKGROUND

Alkene metathesis (olefin metathesis) is a reaction between alkenes or olefinic groups, in which formally alkylidene groups are exchanged between the alkenes or olefinic groups. Examples of metathesis reactions include cross-metathesis, i.e. the reaction between two different olefins forming a new olefin or new olefins, the ring opening metathesis of a cyclic diene, which may also proceed under polymerization, the ring closing metathesis of a diene, the ethenolysis of an olefin having an internal olefinic double bond to form olefins having a terminal olefinic double bonds, and the formation of internal olefin(s) from terminal olefin(s) via homo-metathesis reactions.

US 2011/007742 generally discloses catalysts and processes for the Z-selective formation of internal olefin(s) from terminal olefin(s) via homo-metathesis reactions. The method includes reacting a first molecule having a terminal carbon-carbon double bond and a second, identical molecule via a homo-metathesis reaction to produce a product having an internal carbon-carbon double bond, wherein the internal carbon-carbon double bond of the product includes one carbon atom from the terminal double bond of the first molecule and one carbon atom from the terminal double bond of the second carbon atom, and wherein at least 60% of the internal double bonds of the product are formed as the Z-isomer.

Further compounds based on molybdenum and tungsten and useful as catalysts in metathesis reaction are disclosed in U.S. Pat. No. 6,121,473, US 2008/0119678 and US 2011/0015430. Such catalysts usually are applied or have to be applied in a metathesis reaction in a relatively high molar amount with respect to the molar amount of olefin or olefins in order to achieve a sufficient degree of conversion of the olefin(s) used as starting material. A molar ratio up to 1:500 with respect to the applied olefin(s) (molar ratio catalyst to olefin(s)) may be necessary to achieve a conversion of 30% or more. And because these catalysts may be relatively expensive to make, such low-conversion reactions may not be cost-effective at an industrial scale, and thus may lack industrial applicability. Further, such compounds may be more susceptible to degradation in the presence of certain atmospheric gases. Therefore, they may be difficult to use at a larger scale in an industrial process, where larger quantities may be needed.

Therefore, there is a continuing need to develop organometallic compounds that are stable and that provide relatively high conversion at low catalyst concentrations.

SUMMARY

In a first aspect, the disclosure provides compounds of Formula (I)

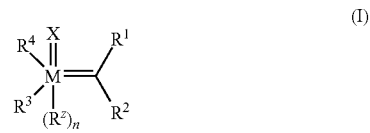

(I)

wherein:

M is a Group 6 metal atom;

X is an oxygen atom, or $=$N—$R^5$, $=$N—N($R^5$)($R^{5'}$), or $=$N—O—$R^5$;

n is 0 or 1;

$R^z$ is a neutral ligand;

$R^1$ is $R^{11}$ or -$G^1$-$R^{11}$;

$R^2$ is $C_{6-18}$ aryl or $C_{4-18}$ heteroaryl, each of which is optionally substituted one or more times by substituents selected independently from $R^6$, wherein any two adjacent $R^6$ optionally combine to form a ring, which is optionally substituted one or more times with substituents selected independently from $R^x$; or $R^2$ is -$G^{10}$-$R^{33}$;

$R^3$ is an anionic ligand, such as —$OR^7$, —$SR^7$, or —N($R^7$)($R^{7'}$);

$R^4$ is pyrrol-1-yl, pyrazol-1-yl, imidazol-1-yl, 1H-1,2,3-triazol-1-yl, 2H-1,2,3-triazol-2-yl, 1H-1,2,4-triazol-1-yl, 4H-1,2,4-triazol-4-yl, indol-1-yl, indazol-1-yl, azaindol-1-yl, —O—$SiR^{21}R^{22}R^{23}$, or —O—$CR^{21}R^{22}R^{23}$, wherein the pyrrolyl, pyrazolyl, imidazolyl, triazolyl, indazolyl, indazolyl, and azaindolyl groups are optionally substituted one or more times with substituents selected independently from $R^8$, wherein any two adjacent $R^8$ optionally combine to form a ring, which is optionally substituted one or more times with substituents selected independently from $R^x$;

$R^5$ is a hydrogen atom, $C_{3-12}$ cycloalkyl, $C_{2-12}$ heterocyclyl, $C_{6-20}$ aryl, $C_{2-20}$ heteroaryl, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^5$ is -$G^5$-$R^{15}$;

$R^{5'}$ is a hydrogen atom, $C_{3-12}$ cycloalkyl, $C_{2-12}$ heterocyclyl, $C_{6-20}$ aryl, $C_{2-20}$ heteroaryl, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^{5'}$ is -$G^5$-$R^{15}$;

$R^6$ is $R^{16}$ or -$G^6$-$R^{16}$;

$R^7$ is a hydrogen atom, $C_{3-12}$ cycloalkyl, $C_{2-12}$ heterocyclyl, $C_{6-20}$ aryl, $C_{2-20}$ heteroaryl, —C(O)—$R^{21}$, —C(O)—$NR^{21}R^{22}$, —$CR^{21}R^{22}R^{23}$, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^7$ is -$G^7$-$R^{17}$;

$R^{7'}$ is a hydrogen atom, $C_{3-12}$ cycloalkyl, $C_{2-12}$ heterocyclyl, $C_{6-20}$ aryl, $C_{2-20}$ heteroaryl, —C(O)—$R^{21}$, —C(O)—NR$^{21}$R$^{22}$, —CR$^{21}$R$^{22}$R$^{23}$, or —SiR$^{21}$R$^{22}$R$^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^{7'}$ is -$G^7$-$R^{17}$;

$R^8$ is $R^{18}$ or -$G^8$-$R^{18}$;

$G^1$, $G^5$, $G^6$, $G^7$, and $G^8$ are independently $C_{1-12}$ alkylene, $C_{2-12}$ alkenylene, or $C_{2-12}$ alkynylene, each of which is optionally substituted one or more times with substituents selected independently from $R^{32}$;

$R^{11}$, $R^{15}$, $R^{16}$, $R^{17}$, and $R^{18}$ are independently a hydrogen atom, a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$-$R^{21}$, —C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, or —O—SiR$^{21}$R$^{22}$R$^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$;

$R^{21}$, $R^{22}$, and $R^{23}$ are independently $R^{28}$ or -$G^9$-$R^{29}$, or when two of $R^{21}$, $R^{22}$, and $R^{23}$ are attached to the same atom, they optionally combine to form a $C_{3-20}$ carbocyclic ring or a $C_{2-20}$ heterocyclic ring, each of which is optionally substituted one or more times with substituents independently from $R^x$;

$G^9$ is $C_{1-12}$ alkylene, $C_{2-12}$ alkenylene, or $C_{2-12}$ alkynylene, each of which is optionally substituted one or more times with substituents selected independently from $R^y$;

$R^{28}$ is $C_{3-12}$ cycloalkyl, $C_{2-12}$ heterocyclyl, $C_{6-20}$ aryl, or $C_{2-20}$ heteroaryl, each of which is optionally substituted one or more times with substituents selected independently from $R^x$; or $R^{28}$ is a hydrogen atom;

$R^{29}$ is a hydrogen atom, $C_{3-12}$ cycloalkyl, $C_{2-12}$ heterocyclyl, $C_{6-20}$ aryl, or $C_{2-20}$ heteroaryl, wherein the cycloalkyl, heterocyclyl, aryl, and heteroaryl groups are optionally substituted one or more times with substituents selected independently from $R^x$;

$R^{31}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, or —O—SiR$^{21}$R$^{22}$R$^{23}$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$, and wherein the alkyl, alkenyl, and alkynyl groups are optionally substituted one or more times with substituents selected independently from $R^{42}$;

$R^{32}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, or —O—SiR$^{21}$R$^{22}$R$^{23}$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$;

$G^{10}$ is —O—, —S—, —Se—, —C(R$^{21}$)(R$^{22}$)—, —Si(R$^{21}$)(R$^{22}$)—, or —N(R$^{21}$)—, wherein the $R^{21}$ of the —NR$^{21}$— group optionally combines with $R^{33}$ to form a nitrogen-containing heterocyclic ring, which is optionally substituted one or more times with substituents selected independently from $R^x$, and wherein any carbon atoms of the nitrogen-containing heterocyclic ring are optionally oxidized to form a carbonyl group;

$R^{33}$ is $C_{2-20}$ heterocyclyl or $C_{2-20}$ heteroaryl, each of which is optionally substituted one or more times by substituents selected independently from $R^{41}$, wherein any two adjacent $R^{41}$ optionally combine to form a ring, which is optionally substituted one or more times with substituents selected independently from $R^x$; or $R^{33}$ is $C_{2-20}$ heteroalkyl, which is optionally substituted one or more times by substituents selected independently from $R^{42}$; or $R^{33}$ is —C(O)—$R^{43}$.

$R^{41}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, or —O—SiR$^{21}$R$^{22}$R$^{23}$, wherein the cycloalkyl, heterocyclyl, aryl, and heteroaryl groups are optionally substituted one or more times with substituents selected independently from $R^x$, and wherein the alkyl, alkenyl, and alkynyl groups are optionally substituted one or more times with substituents selected independently from $R^y$;

$R^{42}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, or —O—SiR$^{21}$R$^{22}$R$^{23}$, wherein the cycloalkyl, heterocyclyl, aryl, and heteroaryl groups are optionally substituted one or more times with substituents selected independently from $R^x$;

$R^{43}$ is $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, or $C_{2-20}$ heteroaryl, wherein the cycloalkyl, heterocyclyl, aryl, and heteroaryl groups are optionally substituted one or more times with substituents selected independently from $R^x$, and wherein the alkyl, alkenyl, and alkynyl groups are optionally substituted one or more times with substituents selected independently from $R^y$;

$R^x$ is a halogen atom, $C_{1-6}$ alkyl, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, or —O—Si($C_{1-6}$ alkyl)$_3$;

$R^y$ is a halogen atom, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, or —O—Si($C_{1-6}$ alkyl)$_3$; and w is 0, 1, or 2;

wherein $R^1$ and $R^2$ optionally combine to form a ring, and $R^2$ and $R^3$ optionally combine to form a ring, and $R^3$ and $R^4$ optionally combine to form a ring;

provided that if $R^3$ is —O—$R^7$, $R^7$ is -$G^7$-$R^{17}$, $G^7$ is alkylene, and $R^{17}$ is a hydrogen atom or a halogen atom, then $R^4$ is not —O—$CR^{21}R^{22}R^{23}$.

In a second aspect, the disclosure provides compounds of Formula (II)

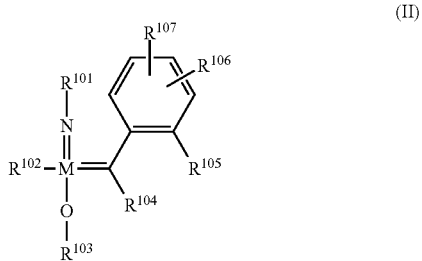

(II)

wherein:

M is a molybdenum atom or a tungsten atom;

$R^{101}$ is aryl, heteroaryl, alkyl, or cycloalkyl, each of which is optionally substituted;

$R^{102}$ is pyrrolyl, imidazolyl, indolyl, pyrazolyl, azaindolyl, or indazolyl, each of which is optionally substituted; or $R^{102}$ is —O—Si(phenyl)$_3$ when $R^{103}$ is —Si(phenyl)$_3$, the phenyl groups being optionally substituted;

$R^{103}$ is $C_{1-6}$ alkyl, $C_{1-6}$ heteroalkyl, aryl, or heteroaryl, each of which is optionally substituted; or $R^{103}$ is tert-butyl, —C(CH$_3$)$_2$(CF$_3$), —C(CF$_3$)$_3$, or —C(CF$_3$)$_2$-(phenyl); or $R^{103}$ is —Si(phenyl)$_3$ when $R^{102}$ is —O—Si(phenyl)$_3$, the phenyl groups being optionally substituted;

$R^{104}$ is a hydrogen atom, $C_{1-6}$ alkyl, or alkoxy;

$R^{105}$ is a hydrogen atom, —O—($C_{1-6}$ alkyl), —CH$_2$—O—($C_{1-6}$ alkyl), heteroalkoxy, or —N($C_{1-6}$ alkyl)$_2$;

$R^{106}$ and $R^{107}$ are independently a hydrogen atom, $C_{1-6}$ alkyl, $C_{1-6}$ alkoxy, a halogen atom, —NO$_2$, amides, or sulfonamides.

In a third aspect, the disclosure provides methods of carrying out a metathesis reaction, including: providing a first compound having one or more carbon-carbon double bonds; and reacting the first compound via a metathesis reaction in the presence of a metathesis catalyst, such as a compound of the first or second aspects disclosed herein. In some embodiments, the first compound has two or more carbon-carbon double bonds. In some such embodiments, the metathesis reaction is a ring-closing metathesis reaction between two of the two or more carbon-carbon double bonds of the first compound.

In a fourth aspect, the disclosure provides methods of carrying out a metathesis reaction, including: providing a first compound having one or more carbon-carbon double bond and a second compound having one or more carbon-carbon double bonds; and reacting the first compound and the second compound via a metathesis reaction in the presence of a metathesis reaction, such as a compound of the first or second aspects disclosed herein. In some embodiments, the first compound and the second compound are the same compound. In some other embodiments, the first compound and the second compound are not the same. In some such embodiments, the first compound is an internal olefin, such as a natural oil. In some embodiments, the second compound is a short-chain alkene, such as ethylene. In some such embodiments, the metathesis reaction yields an amount of 9-decenoic acid or an ester or carboxylate salt thereof.

Further aspects and embodiments are disclosed in greater detail in the foregoing detailed description, examples, and claims, and in any drawings.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any way. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesis," "metathesize," or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms, and "$C_{x\text{-}y}$" refers to a group or compound containing from x to y, inclusive, carbon atoms. For example, "$C_{1\text{-}6}$ alkyl" represents an alkyl group (as defined below) having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4\text{-}10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2\text{-}14}$ range. Such compounds include alpha-olefins, wherein the unsaturated carbon-carbon bond is present at one end of the compound. They may also include dienes or trienes. Low-molecular-weight olefins may also include internal olefins or "low-molecular-weight internal olefins." In certain embodiments, the low-molecular-weight internal olefin is in the $C_{2\text{-}6}$ range. Examples of low-molecular-weight olefins in the $C_{2\text{-}6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7\text{-}9}$ range include 1,4-heptadiene, 1-heptene, 3,6-nonadiene, 3-nonene, 1,4,7-octatriene. Other low-molecular-weight olefins include styrene and vinyl cyclohexane. Olefins in the $C_{2\text{-}10}$ range can also be referred to as "short-chain olefins," which can be either branched or unbranched. In some embodiments, it may be preferable to use a mixture of linear and branched $C_4$ olefins (i.e., combinations of: 1-butene, 2-butene, and/or isobutene).

In some instances, the olefin can be an "alkene," which refers to a straight- or branched-chain non-aromatic hydrocarbon having 2 to 30 carbon atoms and one or more carbon-carbon double bonds, which may be optionally substituted, as herein described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, the term "unsaturated glyceride" refers to mono-, di-, or tri-esters of glycerol, which include one or more carbon-carbon double bonds. For example, in some embodiments, the "unsaturated glyceride" can be represented by the formula R—O—CH$_2$—CH(OR')—CH$_2$(OR''), wherein at least one of R, R', and R'' is a substituted or unsubstituted alkenyl group. In some embodiments, the other group(s) are hydrogen, alkyl, or alkenyl. Examples of unsaturated triglycerides include certain unsaturated fats derived from natural oils.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected independently from nitrogen, oxygen, silicon, selenium, or sulfur, including N-oxides, sulfur oxides, and sulfur dioxides, where feasible), and is referred to as a "heteroalkyl" or a "heteroalkylene" group, respectively.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, 3-butenyl, and 2-hexenyl. In some instances, the "alkenyl" group can be divalent, in which case the group can alternatively be referred to as an "alkenylene" group.

As used herein, "alkynyl" refers to a straight or branched chain non-aromatic hydrocarbon having 2 to 30 carbon atoms and having one or more carbon-carbon triple bonds, which may be optionally substituted, as herein further described, with multiple degrees of substitution being allowed. Examples of "alkynyl," as used herein, include, but are not limited to, ethynyl, 2-propynyl, 2-butynyl, and 3-butynyl. The number of carbon atoms in an alkynyl group is represented by the phrase "$C_{x-y}$ alkynyl," which refers to an alkynyl group, as herein defined, containing from x to y, inclusive, carbon atoms. Thus, "$C_{2-6}$ alkynyl" represents an alkynyl chain having from 2 to 6 carbon atoms and, for example, includes, but is not limited to, ethynyl, 2-propynyl, 2-butynyl, 3-butynyl, and 2-hexynyl. In some instances, the "alkynyl" group can be divalent, in which case the group can alternatively be referred to as an "alkynylene" group.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. The number of carbon atoms in a cycloalkyl group is represented by the phrase "$C_{x-y}$ cycloalkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group. Cycloalkyl and cycloalkylene groups can also be referred to herein as "carbocyclic rings." Also, in some instances, one or more of the carbon atoms in the cycloalkyl or cycloalkylene group can be replaced by a heteroatom (e.g., selected independently from nitrogen, oxygen, silicon, or sulfur, including N-oxides, sulfur oxides, and sulfur dioxides, where feasible), and is referred to as a "heterocyclyl" or "heterocyclylene" group, respectively. The term "heterocyclic ring" can also be used interchangeable with either of these terms. In some embodiments, the cycloalkyl and heterocyclyl groups are fully saturated. In some other embodiments, the cycloalkyl and heterocyclyl groups can contain one or more carbon-carbon double bonds.

As used herein, "aryl" refers to a 6- to 30-membered cyclic, aromatic hydrocarbon, which may be optionally substituted as herein further described, with multiple degrees of substitution being allowed. Examples of "aryl" groups, as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s). In some embodiments, the aryl group, as used herein, is selected from the group consisting of phenyl, 1-naphthyl, and 2-naphthyl, each of which is optionally substituted, as further described herein. Further, in some embodiments, the "aryl" group refers to a ring system that includes only aromatic rings.

As used herein, the term "heteroaryl" refers to a 5- to 30-membered mono- or polycyclic ring system, which contains at least one aromatic ring and also contains one or more heteroatoms, such as oxygen, nitrogen, silicon, or sulfur. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteroaryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, "alkoxy" or "alkyloxy" refer to —OR, where R is an alkyl group (as defined above). The number of carbon atoms in an alkyl group is represented by the phrase "$C_{x\text{-}y}$ alkoxy," which refers to an alkoxy group having an alkyl group, as herein defined, having from x to y, inclusive, carbon atoms.

As used herein, "halogen atom" or "halo" refers to a fluorine, chlorine, bromine, or iodine atom. In some embodiments, the terms refer to a fluorine or chlorine atom. As used herein, "haloalkyl" or "haloalkoxy" refer to alkyl or alkoxy groups, respectively, (as defined above) substituted by one or more times by halogen atoms.

The term "Group 6 metal atom" refers to a chromium, molybdenum, tungsten, or seaborgium atom. In some embodiments, the term refers to a chromium, molybdenum, or tungsten atom. In some further embodiments, the term refers to a tungsten or molybdenum atom.

The term "azaindole" or its variants refers to 4-azaindole, 5-azaindole, 6-azaindole, and 7-azaindole, collectively. In some embodiments, the term refers to 7-azaindole. In some other embodiments, the term refers to 6-azaindole. In some other embodiments, the term refers to 5-azaindole. In some other embodiments, the term refers to 4-azaindole.

The term "ring" refers to any ring system, including bicyclic and tricyclic ring systems, and fused ring systems. In some instances, the phrase "wherein any two adjacent R (i.e., substituents) optionally combine to form a ring" refers to two adjacent substituents bonding together to form a ring system that at least includes bond(s) between the two substituted atoms. For example, substituents at the 3- and 4-positions on a phenyl ring optionally combine to form a four-membered carbocyclic ring (i.e., a 5,6,7,8-tetrahydronaphthyl group). "Adjacent" substituents need not be immediately adjacent, as long as the resulting ring formation yields a stable moiety.

As used herein, "substituted" refers to substitution of one or more hydrogen atoms of the designated moiety with the named non-hydrogen substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for catalyzing a reaction between two olefins. As used herein, the phrases "substituted with one or more . . ." or "substituted one or more times . . ." refer to a number of substituents that equals from one to the maximum number of substituents possible based on the number of available bonding sites, provided that the above conditions of stability and chemical feasibility are met. Further, phrases such as "substituted one or more times by substituents selected independently from R" means that the identity of the one or more substituents are, for each point of substitution, to be selected from the list of substituents recited for R. In this instance, the term "independently" implies that, in cases where two or more substitutions occur, the identity of one substituent selected from R is unaffected by the identity of other substituents selected from R.

As used herein, the term "anionic ligand" refers to a ligand that is anionic, with respect to charge, when formally removed from the metal in its closed-shell electronic state. In some embodiments, the anionic ligand has a −1 charge when formally removed from the metal in its closed-shell electronic state.

As used herein, the term "neutral ligand" refers to a ligand that is neutral, with respect to charge, when formally removed from the metal in its closed-shell electronic state.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compounds or compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Unless otherwise indicated, when various terms are combined to name a substituent, the earlier named feature is farther from the point of attachment. For example, the term "alkyloxymethyl" refers to a substituent having the following structure: —$CH_2$—O—($C_{1-6}$ alkyl).

Other terms are defined in other portions of this description, even though not included in this subsection.

Group 6 Metal Complexes

In at least one aspect, the disclosure provides Group 6 metal complexes, which, among other uses, are suitable for use as catalyst compounds, e.g., catalysts for olefin metathesis reactions. In at least one aspect, the disclosure provides compounds of Formula (I)

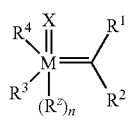

(I)

wherein:

M is a Group 6 metal atom;

X is an oxygen atom, or =N—$R^5$, =N—N($R^5$)($R^{5'}$), or =N—O—$R^5$;

n is 0 or 1;

$R^z$ is a neutral ligand;

$R^1$ is $R^{11}$ or -$G^1$-$R^{11}$;

$R^2$ is $C_{6-18}$ aryl or $C_{4-18}$ heteroaryl, each of which is optionally substituted one or more times by substituents selected independently from $R^6$, wherein any two adjacent $R^6$ optionally combine to form a ring, which is optionally substituted one or more times with substituents selected independently from $R^x$; or $R^2$ is -$G^{10}$-$R^{33}$;

$R^3$ is an anionic ligand, such as —$OR^7$, —$SR^7$, or —N($R^7$)($R^7$);

$R^4$ is pyrrol-1-yl, pyrazol-1-yl, imidazol-1-yl, 1H-1,2,3-triazol-1-yl, 2H-1,2,3-triazol-2-yl, 1H-1,2,4-triazol-1-yl, 4H-1,2,4-triazol-4-yl, indol-1-yl, indazol-1-yl, azaindol-1-yl, —O—$SiR^{21}R^{22}R^{23}$, or —O—$CR^{21}R^{22}R^{23}$, wherein the pyrrolyl, pyrazolyl, imidazolyl, triazolyl, indolyl, indazolyl, and azaindolyl groups are optionally substituted one or more times with substituents selected independently from $R^8$, wherein any two adjacent $R^8$ optionally combine to form a ring, which is optionally substituted one or more times with substituents selected independently from $R^x$;

$R^5$ is a hydrogen atom, $C_{3-12}$ cycloalkyl, $C_{2-12}$ heterocyclyl, $C_{6-20}$ aryl, $C_{2-20}$ heteroaryl, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^5$ is -$G^5$-$R^{15}$;

$R^{5'}$ is a hydrogen atom, $C_{3-12}$ cycloalkyl, $C_{2-12}$ heterocyclyl, $C_{6-20}$ aryl, $C_{2-20}$ heteroaryl, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^{5'}$ is -$G^5$-$R^{15}$;

$R^6$ is $R^{16}$ or -$G^6$-$R^{16}$;

$R^7$ is a hydrogen atom, $C_{3-12}$ cycloalkyl, $C_{2-12}$ heterocyclyl, $C_{6-20}$ aryl, $C_{2-20}$ heteroaryl, —C(O)—$R^{21}$, —C(O)—$NR^{21}R^{22}$, —$CR^{21}R^{22}R^{23}$, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^7$ is -$G^7$-$R^{17}$;

$R^{7'}$ is a hydrogen atom, $C_{3-12}$ cycloalkyl, $C_{2-12}$ heterocyclyl, $C_{6-20}$ aryl, $C_{2-20}$ heteroaryl, —C(O)—$R^{21}$, —C(O)—$NR^{21}R^{22}$, —$CR^{21}R^{22}R^{23}$, or —$SiR^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^{7'}$ is -$G^7$-$R^{17}$;

$R^8$ is $R^{18}$ or -$G^8$-$R^{18}$;

$G^1$, $G^5$, $G^6$, $G^7$, and $G^8$ are independently $C_{1-12}$ alkylene, $C_{2-12}$ alkenylene, or $C_{2-12}$ alkynylene, each of which is optionally substituted one or more times with substituents selected independently from $R^{32}$;

$R^{11}$, $R^{15}$, $R^{16}$, $R^{17}$, and $R^{18}$ are independently a hydrogen atom, a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —$SO_2$—O—$R^{21}$, —O—$SO_2$—$R^{21}$, —C(O)—$R^{21}$, —O—C(O)—$R^{21}$, —O—C(O)—$R^{21}$, —O—C(O)—O—$R^{21}$, —$NR^{21}R^{22}$, —C(O)—$NR^{21}R^{22}$, —N($R^{21}$)—C(O)—$R^{22}$, —N($R^{21}$)—C(O)—O—$R^{22}$, —O—C(O)—$NR^{21}R^{22}$, —N($R^{21}$)—C(O)—$NR^{22}R^{23}$, —$SO_2$—$NR^{21}R^{22}$, —N($R^{21}$)—$SO_2$—$R^{22}$, —$SiR^{21}R^{22}R^{23}$, —O—$SiR^{21}R^{22}R^{23}$, or —$NO_2$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$;

$R^{21}$, $R^{22}$, and $R^{23}$ are independently $R^{28}$ or -$G^9$-$R^{29}$, or when two of $R^{21}$, $R^{22}$, and $R^{23}$ are attached to the same atom, they optionally combine to form a $C_{3-20}$ carbocyclic ring or a $C_{2-20}$ heterocyclic ring, each of which is optionally substituted one or more times with substituents selected independently from $R^x$;

$G^9$ is $C_{1-12}$ alkylene, $C_{2-12}$ alkenylene, or $C_{2-12}$ alkynylene, each of which is optionally substituted one or more times with substituents selected independently from $R^y$;

$R^{28}$ is $C_{3-12}$ cycloalkyl, $C_{2-12}$ heterocyclyl, $C_{6-20}$ aryl, or $C_{2-20}$ heteroaryl, each of which is optionally substituted one or more times with substituents selected independently from $R^x$; or $R^{28}$ is a hydrogen atom;

$R^{29}$ is a hydrogen atom, a halogen atom, $C_{3-12}$ cycloalkyl, $C_{2-12}$ heterocyclyl, $C_{6-20}$ aryl, or $C_{2-20}$ heteroaryl, wherein the cycloalkyl, heterocyclyl, aryl, and heteroaryl groups are optionally substituted one or more times with substituents selected independently from $R^x$;

$R^{31}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, —O—SiR$^{21}$R$^{22}$R$^{23}$, or —NO$_2$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$, and wherein the alkyl, alkenyl, and alkynyl groups are optionally substituted one or more times with substituents selected independently from $R^{42}$;

$R^{32}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, —O—SiR$^{21}$R$^{22}$R$^{23}$, or —NO$_2$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$;

$G^{10}$ is —O—, —S—, —Se—, —C(R$^{21}$)(R$^{22}$)—, —Si(R$^{21}$)(R$^{22}$)—, or —N(R$^{21}$)—, wherein the $R^{21}$ of the —NR$^{21}$— group optionally combines with $R^{33}$ to form a nitrogen-containing heterocyclic ring, which is optionally substituted one or more times with substituents selected independently from $R^x$, and wherein any carbon atoms of the nitrogen-containing heterocyclic ring are optionally oxidized to form a carbonyl group;

$R^{33}$ is $C_{2-20}$ heterocyclyl or $C_{2-20}$ heteroaryl, each of which is optionally substituted one or more times by substituents selected independently from $R^{41}$, wherein any two adjacent $R^{41}$ optionally combine to form a ring, which is optionally substituted one or more times with substituents selected independently from $R^x$; or $R^{33}$ is $C_{2-20}$ heteroalkyl, which is optionally substituted one or more times by substituents selected independently from $R^{42}$; or $R^{33}$ is —C(O)—$R^{43}$;

$R^{41}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, —O—SiR$^{21}$R$^{22}$R$^{23}$, or —NO$_2$, wherein the cycloalkyl, heterocyclyl, aryl, and heteroaryl groups are optionally substituted one or more times with substituents selected independently from $R^x$, and wherein the alkyl, alkenyl, and alkynyl groups are optionally substituted one or more times with substituents selected independently from $R^y$;

$R^{42}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —NR$^{21}$R$^{22}$, —C(O)—NR$^{21}$R$^{22}$, —N(R$^{21}$)—C(O)—$R^{22}$, —N(R$^{21}$)—C(O)—O—$R^{22}$, —O—C(O)—NR$^{21}$R$^{22}$, —N(R$^{21}$)—C(O)—NR$^{22}$R$^{23}$, —SO$_2$—NR$^{21}$R$^{22}$, —N(R$^{21}$)—SO$_2$—$R^{22}$, —SiR$^{21}$R$^{22}$R$^{23}$, —O—SiR$^{21}$R$^{22}$R$^{23}$, or —NO$_2$, wherein the cycloalkyl, heterocyclyl, aryl, and heteroaryl groups are optionally substituted one or more times with substituents selected independently from $R^x$;

$R^{43}$ is $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, or $C_{2-20}$ heteroaryl, wherein the cycloalkyl, heterocyclyl, aryl, and heteroaryl groups are optionally substituted one or more times with substituents selected independently from $R^x$, and wherein the alkyl, alkenyl, and alkynyl groups are optionally substituted one or more times with substituents selected independently from $R^y$;

$R^x$ is a halogen atom, $C_{1-6}$ alkyl, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, —O—Si($C_{1-6}$ alkyl)$_3$, or —NO$_2$;

$R^y$ is a halogen atom, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, —O—Si($C_{1-6}$ alkyl)$_3$, or —NO$_2$; and w is 0, 1, or 2;

wherein $R^1$ and $R^2$ optionally combine to form a ring, and $R^2$ and $R^3$ optionally combine to form a ring, and $R^3$ and $R^4$ optionally combine to form a ring;

provided that if $R^3$ is —O—$R^7$, $R^7$ is -$G^7$-$R^{17}$, $G^7$ is alkylene, and $R^{17}$ is a hydrogen atom or a halogen atom, then $R^4$ is not —O—CR$^{21}$R$^{22}$R$^{23}$.

In some embodiments of any of the aforementioned embodiments, $R^7$ is a hydrogen atom, $C_{3-12}$ cycloalkyl, $C_{2-12}$ heterocyclyl, $C_{6-20}$ aryl, $C_{2-20}$ heteroaryl, —C(O)—$R^{21}$, —C(O)—NR$^{21}$R$^{22}$, —SiR$^{21}$R$^{22}$R$^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$; or $R^7$ is -$G^7$-$R^{17}$;

In some embodiments of any of the aforementioned embodiments, $R^{29}$ is a hydrogen atom, $C_{3-12}$ cycloalkyl, $C_{2-12}$ heterocyclyl, $C_{6-20}$ aryl, or $C_{2-20}$ heteroaryl, wherein the cycloalkyl, heterocyclyl, aryl, and heteroaryl groups are optionally substituted one or more times with substituents selected independently from $R^x$.

In some embodiments of any of the aforementioned embodiments, $G^{10}$ is —O—, —S—, —Se—, —C($R^{21}$)($R^{22}$)—, —Si($R^{21}$)($R^{22}$)—, or —N($R^{21}$)—.

In some embodiments of any of the aforementioned embodiments, $R^{33}$ is $C_{2-20}$ heterocyclyl or $C_{2-20}$ heteroaryl, each of which is optionally substituted one or more times by substituents selected independently from $R^{41}$, wherein any two adjacent $R^{41}$ optionally combine to form a ring, which is optionally substituted one or more times with substituents selected independently from $R^x$; or $R^{33}$ is $C_{2-20}$ heteroalkyl, which is optionally substituted one or more times by substituents selected independently from $R^{42}$.

In some embodiments of any of the aforementioned embodiments, $R^{11}$, $R^{15}$, $R^{16}$, $R^{17}$ and $R^{18}$ are independently a hydrogen atom, a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —N$R^{21}R^{22}$, —C(O)—N$R^{21}R^{22}$, —N($R^{21}$)—C(O)—$R^{22}$, —N($R^{21}$)—C(O)—O—$R^{22}$, —O—C(O)—N$R^{21}R^{22}$, —N($R^{21}$)—C(O)—N$R^{22}R^{23}$, —SO$_2$—N$R^{21}R^{22}$, —N($R^{21}$)—SO$_2$—$R^{22}$, —Si$R^{21}R^{22}R^{23}$, or —O—Si$R^{21}R^{22}R^{23}$, wherein the cycloalkyl, heterocyclyl, aryl, and heteroaryl groups are optionally substituted one or more times with substituents selected independently from $R^{31}$, wherein any two adjacent $R^{31}$ optionally combine to form a ring, which is optionally substituted one or more times with substituents selected independently from $R^x$.

In some embodiments of any of the aforementioned embodiments, $R^{31}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —N$R^{21}R^{22}$, —C(O)—N$R^{21}R^{22}$, —N($R^{21}$)—C(O)—$R^{22}$, —N($R^{21}$)—C(O)—O—$R^{22}$, —O—C(O)—N$R^{21}R^{22}$, —N($R^{21}$)—C(O)—N$R^{22}R^{23}$, —SO$_2$—N$R^{21}R^{22}$, —N($R^{21}$)—SO$_2$—$R^{22}$, —Si$R^{21}R^{22}R^{23}$, or —O—Si$R^{21}R^{22}R^{23}$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$, and wherein the alkyl, alkenyl, and alkynyl groups are optionally substituted one or more times with substituents selected independently from $R^{42}$.

In some embodiments of any of the aforementioned embodiments, $R^{32}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —N$R^{21}R^{22}$, —C(O)—N$R^{21}R^{22}$, —N($R^{21}$)—C(O)—$R^{22}$, —N($R^{21}$)—C(O)—O—$R^{22}$, —O—C(O)—N$R^{21}R^{22}$, —N($R^{21}$)—C(O)—N$R^{22}R^{23}$, —SO$_2$—N$R^{21}R^{22}$, —N($R^{21}$)—SO$_2$—$R^{22}$, —Si$R^{21}R^{22}R^{23}$, or —O—Si$R^{21}R^{22}R^{23}$, wherein the cycloalkyl, heterocyclyl, aryl, and heteroaryl groups are optionally substituted one or more times with substituents selected independently from $R^{41}$, wherein any two adjacent $R^{41}$ optionally combine to form a ring, which is optionally substituted one or more times with substituents selected independently from $R^x$.

In some embodiments of any of the aforementioned embodiments, $R^{41}$ is a halogen atom, $C_{1-12}$ alkyl, $C_{2-12}$ alkenyl, $C_{2-12}$ alkynyl, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —N$R^{21}R^{22}$, —C(O)—N$R^{21}R^{22}$, —N($R^{21}$)—C(O)—$R^{22}$, —N($R^{21}$)—C(O)—O—$R^{22}$, —O—C(O)—N$R^{21}R^{22}$, —N($R^{21}$)—C(O)—N$R^{22}R^{23}$, —SO$_2$—N$R^{21}R^{22}$, —N($R^{21}$)—SO$_2$—$R^{22}$, —Si$R^{21}R^{22}R^{23}$, or —O—Si$R^{21}R^{22}R^{23}$, wherein the cycloalkyl, heterocyclyl, aryl, and heteroaryl groups are optionally substituted one or more times with substituents selected independently from $R^x$, and wherein the alkyl, alkenyl, and alkynyl groups are optionally substituted one or more times with substituents selected independently from $R^y$.

In some embodiments of any of the aforementioned embodiments, $R^{42}$ is a halogen atom, $C_{3-12}$ cycloalkyl, $C_{2-12}$ heterocyclyl, $C_{6-20}$ aryl, $C_{2-20}$ heteroaryl, —CN, —O—$R^{21}$, —S(O)$_w$—$R^{21}$, —SO$_2$—O—$R^{21}$, —O—SO$_2$—$R^{21}$, —C(O)—$R^{21}$, —O—C(O)—$R^{21}$, —O—C(O)—$R^{21}$, —O—C(O)—O—$R^{21}$, —N$R^{21}R^{22}$, —C(O)—N$R^{21}R^{22}$, —N($R^{21}$)—C(O)—$R^{22}$, —N($R^{21}$)—C(O)—O—$R^{22}$, —O—C(O)—N$R^{21}R^{22}$, —N($R^{21}$)—C(O)—N$R^{22}R^{23}$, —SO$_2$—N$R^{21}R^{22}$, —N($R^{21}$)—SO$_2$—$R^{22}$, —Si$R^{21}R^{22}R^{23}$, or —O—Si$R^{21}R^{22}R^{23}$, wherein the cycloalkyl, heterocyclyl, aryl, and heteroaryl groups are optionally substituted one or more times with substituents selected independently from $R^x$.

In some embodiments of any of the aforementioned embodiments, $R^x$ is a halogen atom, $C_{1-6}$ alkyl, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, or —O—Si($C_{1-6}$ alkyl)$_3$.

In some embodiments of any of the aforementioned embodiments, $R^y$ is a halogen atom, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, or —O—Si($C_{1-6}$ alkyl)$_3$.

In some embodiments of any of the aforementioned embodiments, M is a chromium atom, a molybdenum atom, or a tungsten atom. In some such embodiments of any of the aforementioned embodiments, M is a molybdenum atom or a tungsten atom. In some embodiments of any of the aforementioned embodiments, M is a molybdenum atom. In some embodiments of any of the aforementioned embodiments, M is a tungsten atom.

In some further embodiments of any of the aforementioned embodiments, n is 1. In some other embodiments of any of the aforementioned embodiments, n is 0.

In some further embodiments of any of the aforementioned embodiments, X is an oxygen atom. In some other embodiments of any of the aforementioned embodiments, X is =N—$R^5$. In some other embodiments of any of the aforementioned embodiments, X is =N—N($R^5$)($R^{5'}$). In some other embodiments of any of the aforementioned embodiments, X is =N—O—$R^5$. In some embodiments of any of the aforementioned embodiments, $R^5$ and $R^{5'}$ are independently $C_{3-12}$ cycloalkyl, $C_{6-20}$ aryl, or $C_{2-20}$ heteroaryl, each of which is optionally substituted one or more times with substituents selected independently from $R^{31}$, wherein any two adjacent $R^{31}$ optionally combine to form a ring, which is optionally substituted one or more times with substituents selected independently from $R^x$. In some further embodiments of any of the aforementioned embodiments, $R^5$ and $R^{5'}$ are independently $C_{3-12}$ cycloalkyl, phenyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, or 2-pyrazinyl, each of which is optionally substituted one or more times with substituents selected independently from $R^{31}$ wherein any two adjacent $R^{31}$ optionally combine to form a ring, which is optionally substituted one or more times with substituents selected independently from $R^x$. In some further embodiments of any of the aforementioned embodiments, $R^5$ and $R^{5'}$ are independently $C_{3-12}$ cycloalkyl, phenyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, or 2-pyrazinyl, each of which is optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, and —O—Si($C_{1-6}$ alkyl)$_3$. In some further embodiments of any of the aforementioned embodiments, $R^5$ and $R^{5'}$ are independently $C_{3-12}$ cycloalkyl or phenyl, each of which is optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SO$_2$($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —Si($C_{1-6}$ alkyl)$_3$, and —O—Si($C_{1-6}$ alkyl)$_3$. In some further embodiments of any of the aforementioned embodiments, $R^5$ and $R^{5'}$ are independently $C_{3-12}$ cycloalkyl or phenyl, each of which is optionally substituted one or more times by substituents selected independently from the group consisting of a halogen atom and $C_{1-6}$ alkyl. In some further embodiments of any of the aforementioned embodiments, $R^5$ and $R^{5'}$ are independently adamantyl or phenyl, each of which is optionally substituted one or more times by substituents selected independently from the group consisting of a halogen atom and $C_{1-6}$ alkyl. In some further embodiments of any of the aforementioned embodiments, $R^5$ and $R^{5'}$ are independently 1-adamantyl, which is optionally substituted one or more times by substituents selected independently from the group consisting of a halogen atom and $C_{1-6}$ alkyl. In some further embodiments of any of the aforementioned embodiments, $R^5$ and $R^{5'}$ are independently phenyl, which is optionally substituted one or more times by substituents selected independently from the group consisting of a halogen atom and $C_{1-6}$ alkyl. In some embodiments of any of the aforementioned embodiments, the phenyl group is substituted at the 2 and 6 positions, for example, with substituents selected independently from the group consisting of a halogen atom and a $C_{1-6}$ alkyl group. In some further embodiments of any of the aforementioned embodiments, the phenyl group is substituted at the 2 and 6 positions, for example, with substituents selected independently from the group consisting of a chlorine atom, a methyl group, an ethyl group, and an isopropyl group. In some further embodiments of any of the aforementioned embodiments, the substituents at the 2 and 6 positions on the phenyl are the same; in other embodiments of any of the aforementioned embodiments, they are different. In some further embodiments of any of the aforementioned embodiments, $R^5$ and $R^{5'}$ are independently selected independently from the group consisting of phenyl, 2,6-dimethylphenyl, 2,6-dichlorophenyl, and 2,6-diisopropylphenyl. In some further embodiments of any of the aforementioned embodiments, $R^5$ and $R^{5'}$ are independently selected independently from the group consisting of 2,6-dimethylphenyl, 2,6-dichlorophenyl, and 2,6-diisopropylphenyl.

In some further embodiments of any of the aforementioned embodiments, $R^1$ is hydrogen, $C_{1-6}$ alkyl, or —O—($C_{1-6}$ alkyl). In some embodiments of any of the aforementioned embodiments, $R^1$ is a hydrogen atom. In some other embodiments of any of the aforementioned embodiments, $R^1$ is $C_{1-6}$ alkyl, such as methyl, ethyl, or isopropyl. In some other embodiments of any of the aforementioned embodiments, $R^1$ is —O—($C_{1-6}$ alkyl), such as methoxy, ethoxy, or isopropoxy.

In some further embodiments of any of the aforementioned embodiments, $R^2$ is phenyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, or 2-pyrazinyl, each of which is optionally substituted one or more times by substituents selected independently from $R^6$, wherein any two adjacent $R^6$ optionally combine to form a ring, which is optionally substituted one or more times by substituents selected independently from $R^x$. In some further embodiments of any of the aforementioned embodiments, $R^2$ is phenyl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, or 2-pyrazinyl, each of which is optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SH, —S($C_{1-6}$ alkyl), —C(O)—($C_{1-6}$ alkyl), —CHO, —O—C(O)—($C_{1-6}$ alkyl), —C(O)—O—($C_{1-6}$ alkyl), —CO$_2$H, —O—C(O)—O—($C_{1-6}$ alkyl), —SO$_2$($C_{1-6}$ alkyl), —O—SO$_2$($C_{1-6}$ alkyl), —SO$_2$—O($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —NH—CO$_2$H, —N($C_{1-6}$ alkyl)-CO$_2$H, —NH—C(O)—O($C_{1-6}$ alkyl), —N($C_{1-6}$ alkyl)-C(O)—O—($C_{1-6}$ alkyl), —O—C(O)NH$_2$, —O—C(O)NH($C_{1-6}$ alkyl), —O—C(O)N($C_{1-6}$ alkyl)$_2$, —NH—C(O)NH$_2$, —NH—C(O)NH($C_{1-6}$ alkyl), —NH—C(O)N($C_{1-6}$ alkyl)$_2$, —N($C_{1-6}$ alkyl)-C(O)NH$_2$, —N($C_{1-6}$ alkyl)-C(O)NH($C_{1-6}$ alkyl), —N($C_{1-6}$ alkyl)-C(O)N($C_{1-6}$ alkyl)$_2$, —Si($C_{1-6}$ alkyl)$_3$, —O—Si($C_{1-6}$ alkyl)$_3$, —($C_{1-6}$ alkylene)-$C_{3-10}$ cycloalkyl, —($C_{1-6}$ alkylene)-phenyl, —($C_{1-6}$ alkylene)-CN, —($C_{1-6}$ alkylene)-OH, —($C_{1-6}$ alkylene)-O($C_{1-6}$ alkyl), —($C_{1-6}$ alkylene)-SH, —($C_{1-6}$ alkylene)-S($C_{1-6}$ alkyl), —($C_{1-6}$ alkylene)-C(O)—($C_{1-6}$ alkyl), —($C_{1-6}$ alkylene)-CHO, —($C_{1-6}$ alkylene)-O—C(O)—($C_{1-6}$ alkyl), —($C_{1-6}$ alkylene)-C(O)—O—($C_{1-6}$ alkyl), —($C_{1-6}$ alkylene)-CO$_2$H, —($C_{1-6}$ alkylene)-O—C(O)—O—($C_{1-6}$ alkyl), —($C_{1-6}$ alkylene)-SO$_2$($C_{1-6}$ alkyl), —($C_{1-6}$ alkylene)-O—SO$_2$($C_{1-6}$ alkyl), —($C_{1-6}$ alkylene)-SO$_2$—O($C_{1-6}$ alkyl), —($C_{1-6}$ alkylene)-NH$_2$, —($C_{1-6}$ alkylene)-NH($C_{1-6}$ alkyl), —($C_{1-6}$ alkylene)-N($C_{1-6}$ alkyl)$_2$, —($C_{1-6}$ alkylene)-C(O)NH$_2$, —($C_{1-6}$ alkylene)-C(O)NH($C_{1-6}$ alkyl), —($C_{1-6}$ alkylene)-C(O)N($C_{1-6}$ alkyl)$_2$, —($C_{1-6}$ alkylene)-NH—CO$_2$H, —($C_{1-6}$ alkylene)-N($C_{1-6}$ alkyl)-CO$_2$H, —($C_{1-6}$ alkylene)-NH—C(O)—O($C_{1-6}$ alkyl), —($C_{1-6}$ alkylene)-N($C_{1-6}$ alkyl)-C(O)—O—($C_{1-6}$ alkyl), —($C_{1-6}$ alkylene)-O—C(O)NH$_2$, —($C_{1-6}$ alkylene)-O—C(O)NH($C_{1-6}$ alkyl), —($C_{1-6}$ alkylene)-O—C(O)N($C_{1-6}$ alkyl)$_2$, —($C_{1-6}$ alkylene)-NH—C(O)NH$_2$, —($C_{1-6}$ alkylene)-NH—C(O)NH($C_{1-6}$ alkyl), —($C_{1-6}$ alkylene)-NH—C(O)N($C_{1-6}$ alkyl)$_2$, —($C_{1-6}$ alkylene)-N($C_{1-6}$ alkyl)-C(O)NH$_2$, —($C_{1-6}$ alkylene)-N($C_{1-6}$ alkyl)-C(O)NH($C_{1-6}$ alkyl), —($C_{1-6}$ alkylene)-N($C_{1-6}$ alkyl)-C(O)N($C_{1-6}$ alkyl)$_2$, —($C_{1-6}$ alkylene)-Si($C_{1-6}$ alkyl)$_3$, and —($C_{1-6}$ alkylene)-O—Si($C_{1-6}$ alkyl)$_3$. In some embodiments of any of the aforementioned embodiments, $R^2$ is phenyl, which is optionally substituted one or more times by substituents selected independently from $R^6$, wherein any two adjacent $R^6$ optionally combine to form a ring. In some embodiments of any of the aforementioned embodiments, $R^2$ is phenyl, which is optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SH, —S($C_{1-6}$ alkyl), —C(O)—($C_{1-6}$ alkyl), —CHO, —O—C(O)—($C_{1-6}$ alkyl), —C(O)—O—($C_{1-6}$ alkyl), —CO$_2$H, —O—C(O)—O—($C_{1-6}$ alkyl), —SO$_2$($C_{1-6}$ alkyl), —O—SO$_2$($C_{1-6}$ alkyl), —SO$_2$—O($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —NH—CO$_2$H, —N($C_{1-6}$ alkyl)-CO$_2$H, —NH—C(O)—O($C_{1-6}$ alkyl), —N($C_{1-6}$ alkyl)-C(O)—O—($C_{1-6}$ alkyl), —O—C(O)NH$_2$, —O—C(O)NH($C_{1-6}$ alkyl), —O—C(O)N($C_{1-6}$ alkyl)$_2$, —NH—C(O)NH$_2$, —NH—C(O)NH($C_{1-6}$ alkyl), —NH—C(O)N($C_{1-6}$ alkyl)$_2$, —N($C_{1-6}$ alkyl)-C(O)NH$_2$, —N($C_{1-6}$ alkyl)-C(O)NH($C_{1-6}$ alkyl), —N($C_{1-6}$ alkyl)-C(O)N($C_{1-6}$ alkyl)$_2$, —Si($C_{1-6}$ alkyl)$_3$, —O—Si($C_{1-6}$ alkyl)$_3$, —($C_{1-6}$ alkylene)-$C_{3-10}$ cycloalkyl, —($C_{1-6}$ alkylene)-phenyl, —($C_{1-6}$ alkylene)-CN, —($C_{1-6}$ alkylene)-OH, —($C_{1-6}$ alkylene)-O($C_{1-6}$ alkyl), —($C_{1-6}$ alkylene)-SH, —($C_{1-6}$ alkylene)-S($C_{1-6}$ alkyl), —($C_{1-6}$ alkylene)-C(O)—($C_{1-6}$ alkyl), —($C_{1-6}$ alkylene)-CHO, —($C_{1-6}$ alkylene)-O—C(O)—($C_{1-6}$ alkyl), —($C_{1-6}$ alkylene)-C(O)—O—($C_{1-6}$ alkyl), —($C_{1-6}$ alkylene)-CO$_2$H, —($C_{1-6}$ alkylene)-O—C(O)—O—($C_{1-6}$ alkyl), —($C_{1-6}$ alkylene)-SO$_2$($C_{1-6}$ alkyl), —($C_{1-6}$ alkylene)-O—SO$_2$($C_{1-6}$ alkyl), —($C_{1-6}$ alkylene)-SO$_2$—O($C_{1-6}$ alkyl), —($C_{1-6}$ alkylene)-NH$_2$, —($C_{1-6}$ alkylene)-NH($C_{1-6}$ alkyl), —($C_{1-6}$ alkylene)-N($C_{1-6}$ alkyl)$_2$, —($C_{1-6}$ alkylene)-C(O)NH$_2$, —($C_{1-6}$ alkylene)-C(O)NH($C_{1-6}$ alkyl), —($C_{1-6}$ alkylene)-C(O)N($C_{1-6}$ alkyl)$_2$, —($C_{1-6}$ alkylene)-NH—CO$_2$H, —($C_{1-6}$ alkylene)-N($C_{1-6}$ alkyl)-CO$_2$H, —($C_{1-6}$ alkylene)-NH—C(O)—O($C_{1-6}$ alkyl), —($C_{1-6}$ alkylene)-N($C_{1-6}$ alkyl)-C(O)—O—($C_{1-6}$ alkyl), —($C_{1-6}$ alkylene)-O—C(O)NH$_2$, —($C_{1-6}$ alkylene)-O—C(O)NH($C_{1-6}$ alkyl), —($C_{1-6}$ alkylene)-O—C(O)N($C_{1-6}$ alkyl)$_2$, —($C_{1-6}$ alkylene)-NH—C(O)NH$_2$, —($C_{1-6}$ alkylene)-NH—C(O)NH($C_{1-6}$ alkyl), —($C_{1-6}$ alkylene)-NH—C(O)N($C_{1-6}$ alkyl)$_2$, —($C_{1-6}$ alkylene)-N($C_{1-6}$ alkyl)-C(O)NH$_2$, —($C_{1-6}$ alkylene)-N($C_{1-6}$ alkyl)-C(O)NH($C_{1-6}$ alkyl), —($C_{1-6}$ alkylene)-N($C_{1-6}$ alkyl)-C(O)N($C_{1-6}$ alkyl)$_2$, —($C_{1-6}$ alkylene)-Si($C_{1-6}$ alkyl)$_3$, and —($C_{1-6}$ alkylene)-O—Si($C_{1-6}$ alkyl)$_3$. In some further embodiments of any of the aforementioned embodiments, $R^2$ is phenyl, which is optionally substituted one or more times with substituents selected independently from a halogen atom, —OH, —O($C_{1-6}$ alkyl), —($C_{1-6}$ alkylene)-OH, —($C_{1-6}$ alkylene)-O($C_{1-6}$ alkyl), —NH$_2$, —NH($C_{1-6}$ alkyl), —N($C_{1-6}$ alkyl)$_2$, —($C_{1-6}$ alkylene)-NH$_2$, —($C_{1-6}$ alkylene)-NH($C_{1-6}$ alkyl), —($C_{1-6}$ alkylene)-N($C_{1-6}$ alkyl)$_2$, and —NO$_2$. In some further embodiments of any of the aforementioned embodiments, $R^2$ is phenyl, which is optionally substituted one or more times with substituents selected independently from a halogen atom, —OH, —O($C_{1-6}$ alkyl), —($C_{1-6}$ alkylene)-OH, —($C_{1-6}$ alkylene)-O($C_{1-6}$ alkyl), —NH$_2$, —NH($C_{1-6}$ alkyl), —N($C_{1-6}$ alkyl)$_2$, —($C_{1-6}$ alkylene)-NH$_2$, —($C_{1-6}$ alkylene)-NH($C_{1-6}$ alkyl), and —($C_{1-6}$ alkylene)-N($C_{1-6}$ alkyl)$_2$. In some further embodiments of any of the aforementioned embodiments, $R^2$ is unsubstituted phenyl. In some further embodiments of any of the aforementioned embodiments, $R^2$ is phenyl, which is optionally substituted one or more times by substituents selected independently from a fluorine atom, methyl, methoxy, ethoxy, isopropoxy, methoxymethyl, —N(CH$_3$)$_2$, and —NO$_2$.

In some embodiments of any of the aforementioned embodiments, $R^2$ is 2-pyridyl, which is optionally substituted one or more times by substituents selected independently from $R^6$, wherein any two adjacent $R^6$ optionally combine to form a ring. In some embodiments of any of the aforementioned embodiments, $R^2$ is 2-pyridyl, which is optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SH, —S($C_{1-6}$ alkyl), —C(O)—($C_{1-6}$ alkyl), —CHO, —O—C(O)—($C_{1-6}$ alkyl), —C(O)—O—($C_{1-6}$ alkyl), —CO$_2$H, —O—C(O)—O—($C_{1-6}$ alkyl), —SO$_2$($C_{1-6}$ alkyl), —O—SO$_2$($C_{1-6}$ alkyl), —SO$_2$—O($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —NH—CO$_2$H, —N($C_{1-6}$ alkyl)-CO$_2$H, —NH—C(O)—O($C_{1-6}$ alkyl), —N($C_{1-6}$ alkyl)-C(O)—O—($C_{1-6}$ alkyl), —O—C(O)NH$_2$, —O—C(O)NH($C_{1-6}$ alkyl), —O—C(O)N($C_{1-6}$ alkyl)$_2$, —NH—C(O)NH$_2$, —NH—C(O)NH($C_{1-6}$ alkyl), —NH—C(O)N($C_{1-6}$ alkyl)$_2$, —N($C_{1-6}$ alkyl)-C(O)NH$_2$, —N($C_{1-6}$ alkyl)-C(O)NH($C_{1-6}$ alkyl), —N($C_{1-6}$ alkyl)-C(O)N($C_{1-6}$ alkyl)$_2$, —Si($C_{1-6}$ alkyl)$_3$, —O—Si($C_{1-6}$ alkyl)$_3$, —($C_{1-6}$ alkylene)-$C_{3-10}$ cycloalkyl, —($C_{1-6}$ alkylene)-phenyl, —($C_{1-6}$ alkylene)-CN, —($C_{1-6}$ alkylene)-OH, —($C_{1-6}$ alkylene)-O($C_{1-6}$ alkyl), —($C_{1-6}$ alkylene)-SH, —($C_{1-6}$ alkylene)-S($C_{1-6}$ alkyl), —($C_{1-6}$ alkylene)-C(O)—($C_{1-6}$ alkyl), —($C_{1-6}$ alkylene)-CHO, —($C_{1-6}$ alkylene)-O—C(O)—($C_{1-6}$ alkyl), —($C_{1-6}$ alkylene)-C(O)—O—($C_{1-6}$ alkyl), —($C_{1-6}$ alkylene)-CO$_2$H, —($C_{1-6}$ alkylene)-O—C(O)—O—($C_{1-6}$ alkyl), —($C_{1-6}$ alkylene)-SO$_2$($C_{1-6}$ alkyl), —($C_{1-6}$ alkylene)-O—SO$_2$($C_{1-6}$ alkyl), —($C_{1-6}$ alkylene)-SO$_2$—O($C_{1-6}$ alkyl), —($C_{1-6}$ alkylene)-NH$_2$, —($C_{1-6}$ alkylene)-NH($C_{1-6}$ alkyl), —($C_{1-6}$ alkylene)-N($C_{1-6}$ alkyl)$_2$, —($C_{1-6}$ alkylene)-C(O)NH$_2$, —($C_{1-6}$ alkylene)-C(O)NH($C_{1-6}$ alkyl), —($C_{1-6}$ alkylene)-C(O)N($C_{1-6}$ alkyl)$_2$, —($C_{1-6}$ alkylene)-NH—CO$_2$H, —($C_{1-6}$ alkylene)-N($C_{1-6}$ alkyl)-CO$_2$H, —($C_{1-6}$ alkylene)-NH—C(O)—O($C_{1-6}$ alkyl), —($C_{1-6}$ alkylene)-N($C_{1-6}$ alkyl)-C(O)—O—($C_{1-6}$ alkyl), —($C_{1-6}$ alkylene)-O—C(O)NH$_2$, —($C_{1-6}$ alkylene)-O—C(O)NH($C_{1-6}$ alkyl), —($C_{1-6}$ alkylene)-O—C(O)N($C_{1-6}$ alkyl)$_2$, —($C_{1-6}$ alkylene)-NH—C(O)NH$_2$, —($C_{1-6}$ alkylene)-NH—C(O)NH($C_{1-6}$ alkyl), —($C_{1-6}$ alkylene)-NH—C(O)N($C_{1-6}$ alkyl)$_2$, —($C_{1-6}$ alkylene)-N($C_{1-6}$ alkyl)-C(O)NH$_2$, —($C_{1-6}$ alkylene)-N($C_{1-6}$ alkyl)-C(O)NH($C_{1-6}$ alkyl), —($C_{1-6}$ alkylene)-N($C_{1-6}$ alkyl)-C(O)N($C_{1-6}$ alkyl)$_2$, —($C_{1-6}$ alkylene)-Si($C_{1-6}$ alkyl)$_3$, and —($C_{1-6}$ alkylene)-O—Si($C_{1-6}$ alkyl)$_3$. In some further embodiments of any of the aforementioned embodiments, $R^2$ is 2-pyridyl, which is optionally substituted one or more times with substituents selected independently from a halogen atom, —OH, —O($C_{1-6}$ alkyl), —($C_{1-6}$ alkylene)-OH, —($C_{1-6}$ alkylene)-O($C_{1-6}$ alkyl), —NH$_2$, —NH($C_{1-6}$ alkyl), —N($C_{1-6}$ alkyl)$_2$, —($C_{1-6}$ alkylene)-NH$_2$, —($C_{1-6}$ alkylene)-NH($C_{1-6}$ alkyl), and —($C_{1-6}$ alkylene)-N($C_{1-6}$ alkyl)$_2$. In some embodiments of any of the aforementioned embodiments, $R^2$ is unsubstituted 2-pyridyl.

In some further embodiments of any of the aforementioned embodiments, $R^2$ is 2-($C_{1-6}$ alkyloxy)phenyl, where the phenyl ring is further optionally substituted one or more times by substituents selected independently from the group consisting of a halogen atom, $C_{1-6}$ alkyl, $C_{3-10}$ cycloalkyl, phenyl, —CN, —OH, —O($C_{1-6}$ alkyl), —SH, —S($C_{1-6}$ alkyl), —C(O)—($C_{1-6}$ alkyl), —CHO, —O—C(O)—($C_{1-6}$ alkyl), —C(O)—O—($C_{1-6}$ alkyl), —CO$_2$H, —O—C(O)—O—($C_{1-6}$ alkyl), —SO$_2$($C_{1-6}$ alkyl), —O—SO$_2$($C_{1-6}$ alkyl), —SO$_2$—O($C_{1-6}$ alkyl), —NH$_2$, —NH($C_{1-6}$ alkyl), —N($C_{1-6}$ alkyl)$_2$, —C(O)NH$_2$, —C(O)NH($C_{1-6}$ alkyl), —C(O)N($C_{1-6}$ alkyl)$_2$, —NH—CO$_2$H, —N($C_{1-6}$ alkyl)-CO$_2$H, —NH—C(O)—O($C_{1-6}$ alkyl), —N($C_{1-6}$ alkyl)-C(O)—O—($C_{1-6}$ alkyl), —O—C(O)NH$_2$, —O—C(O)NH(C$_{1-6}$ alkyl), —O—C(O)N(C$_{1-6}$ alkyl)$_2$, —NH—C(O)NH$_2$, —NH—C(O)NH(C$_{1-6}$ alkyl), —NH—C(O)N(C$_{1-6}$ alkyl)$_2$, —N(C$_{1-6}$ alkyl)-C(O)NH$_2$, —N(C$_{1-6}$ alkyl)-C(O)NH(C$_{1-6}$ alkyl), —N(C$_{1-6}$ alkyl)-C(O)N(C$_{1-6}$ alkyl)$_2$, —Si(C$_{1-6}$ alkyl)$_3$, —O—Si(C$_{1-6}$ alkyl)$_3$, —(C$_{1-6}$ alkylene)-C$_{3-10}$ cycloalkyl, —(C$_{1-6}$ alkylene)-phenyl, —(C$_{1-6}$ alkylene)-CN, —(C$_{1-6}$ alkylene)-OH, —(C$_{1-6}$ alkylene)-O(C$_{1-6}$ alkyl), —(C$_{1-6}$ alkylene)-SH, —(C$_{1-6}$ alkylene)-S(C$_{1-6}$ alkyl), —(C$_{1-6}$ alkylene)-C(O)—(C$_{1-6}$ alkyl), —(C$_{1-6}$ alkylene)-CHO, —(C$_{1-6}$ alkylene)-O—C(O)—(C$_{1-6}$ alkyl), —(C$_{1-6}$ alkylene)-C(O)—O—(C$_{1-6}$ alkyl), —(C$_{1-6}$ alkylene)-CO$_2$H, —(C$_{1-6}$ alkylene)-O—C(O)—O—(C$_{1-6}$ alkyl), —(C$_{1-6}$ alkylene)-SO$_2$(C$_{1-6}$ alkyl), —(C$_{1-6}$ alkylene)-O—SO$_2$(C$_{1-6}$ alkyl), —(C$_{1-6}$ alkylene)-SO$_2$—O(C$_{1-6}$ alkyl), —(C$_{1-6}$ alkylene)-NH$_2$, —(C$_{1-6}$ alkylene)-NH(C$_{1-6}$ alkyl), —(C$_{1-6}$ alkylene)-N(C$_{1-6}$ alkyl)$_2$, —(C$_{1-6}$ alkylene)-C(O)NH$_2$, —(C$_{1-6}$ alkylene)-C(O)NH(C$_{1-6}$ alkyl), —(C$_{1-6}$ alkylene)-C(O)N(C$_{1-6}$ alkyl)$_2$, —(C$_{1-6}$ alkylene)-NH—CO$_2$H, —(C$_{1-6}$ alkylene)-N(C$_{1-6}$ alkyl)-CO$_2$H, —(C$_{1-6}$ alkylene)-NH—C(O)—O(C$_{1-6}$ alkyl), —(C$_{1-6}$ alkylene)-N(C$_{1-6}$ alkyl)-C(O)—O—(C$_{1-6}$ alkyl), —(C$_{1-6}$ alkylene)-O—C(O)NH$_2$, —(C$_{1-6}$ alkylene)-O—C(O)NH(C$_{1-6}$ alkyl), —(C$_{1-6}$ alkylene)-O—C(O)N(C$_{1-6}$ alkyl)$_2$, —(C$_{1-6}$ alkylene)-NH—C(O)NH$_2$, —(C$_{1-6}$ alkylene)-NH—C(O)NH(C$_{1-6}$ alkyl), —(C$_{1-6}$ alkylene)-NH—C(O)N(C$_{1-6}$ alkyl)$_2$, —(C$_{1-6}$ alkylene)-N(C$_{1-6}$ alkyl)-C(O)NH$_2$, —(C$_{1-6}$ alkylene)-N(C$_{1-6}$ alkyl)-C(O)NH(C$_{1-6}$ alkyl), —(C$_{1-6}$ alkylene)-N(C$_{1-6}$ alkyl)-C(O)N(C$_{1-6}$ alkyl)$_2$, —(C$_{1-6}$ alkylene)-Si(C$_{1-6}$ alkyl)$_3$, and —(C$_{1-6}$ alkylene)-O—Si(C$_{1-6}$ alkyl)$_3$. In some embodiments of any of the aforementioned embodiments, R$^2$ is 2-(C$_{1-6}$ alkyloxy)phenyl, which is optionally substituted one or more times with substituents selected independently from a halogen atom, —OH, —O(C$_{1-6}$ alkyl), —(C$_{1-6}$ alkylene)-OH, —(C$_{1-6}$ alkylene)-O(C$_{1-6}$ alkyl), —NH$_2$, —NH(C$_{1-6}$ alkyl), —N(C$_{1-6}$ alkyl)$_2$, —(C$_{1-6}$ alkylene)-NH$_2$, —(C$_{1-6}$ alkylene)-NH(C$_{1-6}$ alkyl), and —(C$_{1-6}$ alkylene)-N(C$_{1-6}$ alkyl)$_2$. In some further such embodiments of any of the aforementioned embodiments, R$^2$ is 2-methoxyphenyl, 2-ethoxyphenyl, or 2-isopropoxyphenyl, each of which is optionally substituted as indicated in any of the above embodiments of this paragraph. In some even further embodiments, R$^2$ is 2-methoxyphenyl, which is optionally substituted as indicated in any of the above embodiments. In some further embodiments of any of the aforementioned embodiments, R$^2$ is 2-methoxyphenyl, 2-ethoxyohenyl, or 2-isopropxyphenyl, each of which is optionally substituted one or more times by substituents selected independently from the group consisting of methyl, methoxy, and a fluorine atom. In some embodiments of any of the aforementioned embodiments, R$^2$ is 2-methoxyphenyl, 2-ethoxyphenyl, 2-isopropxyphenyl, 2-methoxy-4-fluorophenyl, 2-methoxy-5-fluorophenyl, 2,4-dimethoxyphenyl, 2,5-dimethoxyphenyl, 2,4,5-trimethoxyphenyl, or 2-methoxy-4-methylphenyl.

In some further embodiments of any of the aforementioned embodiments, R$^2$ is 2-(C$_{1-6}$ alkyloxymethyl)phenyl, where the phenyl ring is further optionally substituted one or more times by substituents selected independently from the group consisting of a halogen atom, C$_{1-6}$ alkyl, C$_{3-10}$ cycloalkyl, phenyl, —CN, —OH, —O(C$_{1-6}$ alkyl), —SH, —S(C$_{1-6}$ alkyl), —C(O)—(C$_{1-6}$ alkyl), —CHO, —O—C(O)—(C$_{1-6}$ alkyl), —C(O)—O—(C$_{1-6}$ alkyl), —CO$_2$H, —O—C(O)—O—(C$_{1-6}$ alkyl), —SO$_2$(C$_{1-6}$ alkyl), —O—SO$_2$(C$_{1-6}$ alkyl), —SO$_2$—O(C$_{1-6}$ alkyl), —NH$_2$, —NH(C$_{1-6}$ alkyl), —N(C$_{1-6}$ alkyl)$_2$, —C(O)NH$_2$, —C(O)NH(C$_{1-6}$ alkyl), —C(O)N(C$_{1-6}$ alkyl)$_2$, —NH—CO$_2$H, —N(C$_{1-6}$ alkyl)-CO$_2$H, —NH—C(O)—O(C$_{1-6}$ alkyl), —N(C$_{1-6}$ alkyl)-C(O)—O—(C$_{1-6}$ alkyl), —O—C(O)NH$_2$, —O—C(O)NH(C$_{1-6}$ alkyl), —O—C(O)N(C$_{1-6}$ alkyl)$_2$, —NH—C(O)NH$_2$, —NH—C(O)NH(C$_{1-6}$ alkyl), —NH—C(O)N(C$_{1-6}$ alkyl)$_2$, —N(C$_{1-6}$ alkyl)-C(O)NH$_2$, —N(C$_{1-6}$ alkyl)-C(O)NH(C$_{1-6}$ alkyl), —N(C$_{1-6}$ alkyl)-C(O)N(C$_{1-6}$ alkyl)$_2$, —Si(C$_{1-6}$ alkyl)$_3$, —O—Si(C$_{1-6}$ alkyl)$_3$, —(C$_{1-6}$ alkylene)-C$_{3-10}$ cycloalkyl, —(C$_{1-6}$ alkylene)-phenyl, —(C$_{1-6}$ alkylene)-CN, —(C$_{1-6}$ alkylene)-OH, —(C$_{1-6}$ alkylene)-O(C$_{1-6}$ alkyl), —(C$_{1-6}$ alkylene)-SH, —(C$_{1-6}$ alkylene)-S(C$_{1-6}$ alkyl), —(C$_{1-6}$ alkylene)-C(O)—(C$_{1-6}$ alkyl), —(C$_{1-6}$ alkylene)-CHO, —(C$_{1-6}$ alkylene)-O—C(O)—(C$_{1-6}$ alkyl), —(C$_{1-6}$ alkylene)-C(O)—O—(C$_{1-6}$ alkyl), —(C$_{1-6}$ alkylene)-CO$_2$H, —(C$_{1-6}$ alkylene)-O—C(O)—O—(C$_{1-6}$ alkyl), —(C$_{1-6}$ alkylene)-SO$_2$(C$_{1-6}$ alkyl), —(C$_{1-6}$ alkylene)-O—SO$_2$(C$_{1-6}$ alkyl), —(C$_{1-6}$ alkylene)-SO$_2$—O(C$_{1-6}$ alkyl), —(C$_{1-6}$ alkylene)-NH$_2$, —(C$_{1-6}$ alkylene)-NH(C$_{1-6}$ alkyl), —(C$_{1-6}$ alkylene)-N(C$_{1-6}$ alkyl)$_2$, —(C$_{1-6}$ alkylene)-C(O)NH$_2$, —(C$_{1-6}$ alkylene)-C(O)NH(C$_{1-6}$ alkyl), —(C$_{1-6}$ alkylene)-C(O)N(C$_{1-6}$ alkyl)$_2$, —(C$_{1-6}$ alkylene)-NH—CO$_2$H, —(C$_{1-6}$ alkylene)-N(C$_{1-6}$ alkyl)-CO$_2$H, —(C$_{1-6}$ alkylene)-NH—C(O)—O(C$_{1-6}$ alkyl), —(C$_{1-6}$ alkylene)-N(C$_{1-6}$ alkyl)-C(O)—O—(C$_{1-6}$ alkyl), —(C$_{1-6}$ alkylene)-O—C(O)NH$_2$, —(C$_{1-6}$ alkylene)-O—C(O)NH(C$_{1-6}$ alkyl), —(C$_{1-6}$ alkylene)-O—C(O)N(C$_{1-6}$ alkyl)$_2$, —(C$_{1-6}$ alkylene)-NH—C(O)NH$_2$, —(C$_{1-6}$ alkylene)-NH—C(O)NH(C$_{1-6}$ alkyl), —(C$_{1-6}$ alkylene)-NH—C(O)N(C$_{1-6}$ alkyl)$_2$, —(C$_{1-6}$ alkylene)-N(C$_{1-6}$ alkyl)-C(O)NH$_2$, —(C$_{1-6}$ alkylene)-N(C$_{1-6}$ alkyl)-C(O)NH(C$_{1-6}$ alkyl), —(C$_{1-6}$ alkylene)-N(C$_{1-6}$ alkyl)-C(O)N(C$_{1-6}$ alkyl)$_2$, —(C$_{1-6}$ alkylene)-Si(C$_{1-6}$ alkyl)$_3$, and —(C$_{1-6}$ alkylene)-O—Si(C$_{1-6}$ alkyl)$_3$. In some embodiments of any of the aforementioned embodiments, R$^2$ is 2-(C$_{1-6}$ alkyloxymethyl)phenyl, which is optionally substituted one or more times with substituents selected independently from a halogen atom, —OH, —O(C$_{1-6}$ alkyl), —(C$_{1-6}$ alkylene)-OH, —(C$_{1-6}$ alkylene)-O(C$_{1-6}$ alkyl), —NH$_2$, —NH(C$_{1-6}$ alkyl), —N(C$_{1-6}$ alkyl)$_2$, —(C$_{1-6}$ alkylene)-NH$_2$, —(C$_{1-6}$ alkylene)-NH(C$_{1-6}$ alkyl), and —(C$_{1-6}$ alkylene)-N(C$_{1-6}$ alkyl)$_2$. In some further embodiments of any of the aforementioned embodiments, R$^2$ is 2-(methoxymethyl)phenyl, 2-(ethoxymethyl)phenyl, or 2-(isopropoxymethyl)phenyl, each of which is optionally substituted as indicated in any of the above embodiments of this paragraph. In some even further embodiments of any of the aforementioned embodiments, R$^2$ is 2-(methoxymethyl)phenyl, which is optionally substituted as indicated in any of the above embodiments of this paragraph. In some further embodiments of any of the aforementioned embodiments, R$^2$ is 2-(methoxymethyl)phenyl.

In some further embodiments of any of the aforementioned embodiments, R$^2$ is 2-[—N(C$_{1-6}$ alkyl)$_2$]phenyl, where the phenyl ring is further optionally substituted one or more times by substituents selected independently from the group consisting of a halogen atom, C$_{1-6}$ alkyl, C$_{3-10}$ cycloalkyl, phenyl, —CN, —OH, —O(C$_{1-6}$ alkyl), —SH, —S(C$_{1-6}$ alkyl), —C(O)—(C$_{1-6}$ alkyl), —CHO, —O—C(O)—(C$_{1-6}$ alkyl), —C(O)—O—(C$_{1-6}$ alkyl), —CO$_2$H, —O—C(O)—O—(C$_{1-6}$ alkyl), —SO$_2$(C$_{1-6}$ alkyl), —O—SO$_2$(C$_{1-6}$ alkyl), —SO$_2$—O(C$_{1-6}$ alkyl), —NH$_2$, —NH(C$_{1-6}$ alkyl), —N(C$_{1-6}$ alkyl)$_2$, —C(O)NH$_2$, —C(O)NH(C$_{1-6}$ alkyl), —C(O)N(C$_{1-6}$ alkyl)$_2$, —NH—CO$_2$H, —N(C$_{1-6}$ alkyl)-CO$_2$H, —NH—C(O)—O(C$_{1-6}$ alkyl), —N(C$_{1-6}$ alkyl)-C(O)—O—(C$_{1-6}$ alkyl), —O—C(O)NH$_2$, —O—C(O)NH(C$_{1-6}$ alkyl), —O—C(O)N(C$_{1-6}$ alkyl)$_2$, —NH—C(O)NH$_2$, —NH—C(O)NH(C$_{1-6}$ alkyl), —NH—C(O)N(C$_{1-6}$ alkyl)$_2$, —N(C$_{1-6}$ alkyl)-C(O)NH$_2$, —N(C$_{1-6}$ alkyl)-C(O)NH(C$_{1-6}$ alkyl), —N(C$_{1-6}$ alkyl)-C(O)N(C$_{1-6}$ alkyl)$_2$, —Si(C$_{1-6}$ alkyl)$_3$, —O—Si(C$_{1-6}$ alkyl)$_3$, —(C$_{1-6}$ alkylene)-C$_{3-10}$ cycloalkyl, —(C$_{1-6}$ alkylene)-phenyl, —(C$_{1-6}$ alkylene)-CN, —(C$_{1-6}$ alkylene)-OH, —(C$_{1-6}$ alkylene)-O(C$_{1-6}$ alkyl), —(C$_{1-6}$ alkylene)-SH, —(C$_{1-6}$ alkylene)-S(C$_{1-6}$ alkyl), —(C$_{1-6}$ alkylene)-C(O)—(C$_{1-6}$ alkyl), —(C$_{1-6}$ alkylene)-CHO, —(C$_{1-6}$ alkylene)-O—C(O)—(C$_{1-6}$ alkyl), —(C$_{1-6}$ alkylene)-C(O)—O—(C$_{1-6}$ alkyl), —(C$_{1-6}$ alkylene)-CO$_2$H, —(C$_{1-6}$ alkylene)-O—C(O)—O—(C$_{1-6}$ alkyl), —(C$_{1-6}$ alkylene)-SO$_2$(C$_{1-6}$ alkyl), —(C$_{1-6}$ alkylene)-O—SO$_2$(C$_{1-6}$ alkyl), —(C$_{1-6}$ alkylene)-SO$_2$—O(C$_{1-6}$ alkyl), —(C$_{1-6}$ alkylene)-NH$_2$, —(C$_{1-6}$ alkylene)-NH(C$_{1-6}$ alkyl), —(C$_{1-6}$ alkylene)-N(C$_{1-6}$ alkyl)$_2$, —(C$_{1-6}$ alkylene)-C(O)NH$_2$, —(C$_{1-6}$ alkylene)-C(O)NH(C$_{1-6}$ alkyl), —(C$_{1-6}$ alkylene)-C(O)N(C$_{1-6}$ alkyl)$_2$, —(C$_{1-6}$ alkylene)-NH—CO$_2$H, —(C$_{1-6}$ alkylene)-N(C$_{1-6}$ alkyl)-CO$_2$H, —(C$_{1-6}$ alkylene)-NH—C(O)—O(C$_{1-6}$ alkyl), —(C$_{1-6}$ alkylene)-N(C$_{1-6}$ alkyl)-C(O)—O—(C$_{1-6}$ alkyl), —(C$_{1-6}$ alkylene)-O—C(O)NH$_2$, —(C$_{1-6}$ alkylene)-O—C(O)NH(C$_{1-6}$ alkyl), —(C$_{1-6}$ alkylene)-O—C(O)N(C$_{1-6}$ alkyl)$_2$, —(C$_{1-6}$ alkylene)-NH—C(O)NH$_2$, —(C$_{1-6}$ alkylene)-NH—C(O)NH(C$_{1-6}$ alkyl), —(C$_{1-6}$ alkylene)-NH—C(O)N(C$_{1-6}$ alkyl)$_2$, —(C$_{1-6}$ alkylene)-N(C$_{1-6}$ alkyl)-C(O)NH$_2$, —(C$_{1-6}$ alkylene)-N(C$_{1-6}$ alkyl)-C(O)NH(C$_{1-6}$ alkyl), —(C$_{1-6}$ alkylene)-N(C$_{1-6}$ alkyl)-C(O)N(C$_{1-6}$ alkyl)$_2$, —(C$_{1-6}$ alkylene)-Si(C$_{1-6}$ alkyl)$_3$, and —(C$_{1-6}$ alkylene)-O—Si(C$_{1-6}$ alkyl)$_3$. In some embodiments of any of the aforementioned embodiments, R$^2$ is 2-(C$_{1-6}$ alkyloxymethyl)phenyl, which is optionally substituted one or more times with substituents selected independently from a halogen atom, —OH, —O(C$_{1-6}$ alkyl), —(C$_{1-6}$ alkylene)-OH, —(C$_{1-6}$ alkylene)-O(C$_{1-6}$ alkyl), —NH$_2$, —NH(C$_{1-6}$ alkyl), —N(C$_{1-6}$ alkyl)$_2$, —(C$_{1-6}$ alkylene)-NH$_2$, —(C$_{1-6}$ alkylene)-NH(C$_{1-6}$ alkyl), and —(C$_{1-6}$ alkylene)-N(C$_{1-6}$ alkyl)$_2$. In some further embodiments of any of the aforementioned embodiments, R$^2$ is 2-(dimethylamino)phenyl, which is optionally substituted as indicated in any of the above embodiments of this paragraph. In some even further embodiments of any of the aforementioned embodiments, R$^2$ is 2-(dimethylamino)phenyl.

In some embodiments of any of the aforementioned embodiments, R$^2$ is -G$^{10}$-R$^{33}$. In some embodiments of any of the aforementioned embodiments, G$^{10}$ is —O—. In some other embodiments of any of the aforementioned embodiments, G$^{10}$ is —S—. In some other embodiments of any of the aforementioned embodiments, G$^{10}$ is —Se—. In some other embodiments of any of the aforementioned embodiments, G$^{10}$ is —C(R$^{21}$)(R$^{22}$)—. In some other embodiments of any of the aforementioned embodiments, G$^{10}$ is —Si(R$^{21}$)(R$^{22}$). In some other embodiments of any of the aforementioned embodiments, G$^{10}$ is —N(R$^{21}$)—.

In some further such embodiments of any of the aforementioned embodiments, R$^{33}$ is C$_{2-20}$ heterocyclyl, which is optionally substituted one or more times by substituents selected independently from R$^{41}$, wherein any two adjacent R$^{41}$ optionally combine to form a ring, which is optionally substituted one or more times with substituents selected independently from R$^x$. In some embodiments of any of the aforementioned embodiments, the heterocyclyl group has a heteroatom at the 2-position relative to the attachment point of the heterocyclyl group to G$^{10}$, wherein said heteroatom is an oxygen atom, a sulfur atom, a selenium atom, or a nitrogen atom. In some embodiments of any of the aforementioned embodiments, said heteroatom is an oxygen atom. In some other embodiments of any of the aforementioned embodiments, said heteroatom is a sulfur atom. In some other embodiments of any of the aforementioned embodiments, said heteroatom is a nitrogen atom.

In some embodiments of any of the aforementioned embodiments, R$^{33}$ is 2-tetrahydropyranyl, which is optionally substituted one or more times by substituents selected independently from R$^{41}$, wherein any two adjacent R$^{41}$ optionally combine to form a ring, which is optionally substituted one or more times with substituents selected independently from R$^x$. In some embodiments of any of the aforementioned embodiments, R$^{33}$ is unsubstituted 2-tetrahydropyranyl.

In some further such embodiments of any of the aforementioned embodiments, R$^{33}$ is C$_{2-20}$ heteroaryl, which is optionally substituted one or more times by substituents selected independently from R$^{41}$, wherein any two adjacent R$^{41}$ optionally combine to form a ring, which is optionally substituted one or more times with substituents selected independently from R$^x$. In some embodiments of any of the aforementioned embodiments, the heteroaryl group has a heteroatom at the 2-position relative to the attachment point of the heteroaryl group to G$^{10}$, wherein said heteroatom is an oxygen atom, a sulfur atom, a selenium atom, or a nitrogen atom. In some embodiments of any of the aforementioned embodiments, said heteroatom is a nitrogen atom.

In some embodiments of any of the aforementioned embodiments, R$^{33}$ is 2-pyridyl, which is optionally substituted one or more times by substituents selected independently from R$^{41}$, wherein any two adjacent R$^{41}$ optionally combine to form a ring, which is optionally substituted one or more times with substituents selected independently from R$^x$. In some embodiments of any of the aforementioned embodiments, R$^{33}$ is unsubstituted 2-pyridyl.

In some further such embodiments of any of the aforementioned embodiments, R$^{33}$ is C$_{2-20}$ heteroalkyl, which is optionally substituted one or more times by substituents selected independently from R$^{42}$. In some embodiments of any of the aforementioned embodiments, the heteroalkyl group has a heteroatom at the 2-position relative to the attachment point of the heteroalkyl group to G$^{10}$, wherein said heteroatom is an oxygen atom, a sulfur atom, a selenium atom, or a nitrogen atom. In some embodiments of any of the aforementioned embodiments, said heteroatom is an oxygen atom. In some other such embodiments of any of the aforementioned embodiments, said heteroatom is a sulfur atom. In some other embodiments of any of the aforementioned embodiments, said heteroatom is a nitrogen atom.

In some embodiments of any of the aforementioned embodiments, R$^{33}$ is —CH$_2$—O—(C$_{1-10}$ alkyl), —CH(C$_{1-6}$ alkyl)-O—(C$_{1-10}$ alkyl), or —C(C$_{1-6}$ alkyl)$_2$-O—(C$_{1-6}$ alkyl).

In some embodiments of any of the aforementioned embodiments, G$^{10}$ is —NR$^{21}$— and the R$^{21}$ group combines with R$^{33}$ to form a nitrogen-containing heterocyclic ring, which is optionally substituted one or more times with substituents selected independently from R$^x$, and wherein any carbon atom of the ring is optionally oxidized to form a carbonyl group. In some such embodiments of any of the aforementioned embodiments, one carbon atom immediately adjacent to the nitrogen atom is oxidized to form a carbonyl group. In some embodiments of any of the aforementioned embodiments, R$^2$ is pyrrolidin-2-on-1-yl, imidazolidin-2-on-1-yl, imidazolidin-5-on-1-yl, or piperidin-2-on-1-yl. In some embodiments of any of the aforementioned embodiments, R$^2$ is pyrrolidin-2-on-1-yl.

In some embodiments of any of the aforementioned embodiments, R$^{33}$ is —C(O)—R$^{43}$. In some further embodiments of any of the aforementioned embodiments, R$^{43}$ is C$_{1-6}$ alkyl. In some further embodiments of any of the aforementioned embodiments, R$^{43}$ is methyl, ethyl, isopropyl, propyl, butyl, isobutyl, sec-butyl, or tert-butyl. In some further embodiments of any of the aforementioned embodiments $R^{43}$ is methyl or tert-butyl. In some further embodiments of any of the aforementioned embodiments, $R^{43}$ is phenyl.

In some further embodiments of any of the aforementioned embodiments, $R^3$ is —$OR^7$, —$SR^7$, or —$N(R^7)(R^{7'})$. In some further embodiments of any of the aforementioned embodiments, $R^3$ is —$OR^7$ or —$SR^7$. In some embodiments of any of the aforementioned embodiments, $R^3$ is —$SR^7$. In some other embodiments of any of the aforementioned embodiments, $R^3$ is —$OR^7$. In some other embodiments of any of the aforementioned embodiments, $R^3$ is —$N(R^7)(R^{7'})$. In some embodiments of any of the aforementioned embodiments, $R^7$ is -$G^7$-$R^{17}$. In some further embodiments of any of the aforementioned embodiments, -$G^7$-$R^{17}$ is $C_{1-12}$ alkyl, which is optionally substituted one or more times with substituents selected independently from $R^{32}$. In some even further embodiments of any of the aforementioned embodiments, -$G^7$-$R^{17}$ is $C_{1-12}$ alkyl, which is optionally substituted one or more times with substituents selected independently from the group consisting of a halogen atom and phenyl, wherein the phenyl group is optionally substituted one or more times with substituents selected independently from the group consisting of a halogen atom, $C_{1-6}$ alkyl, —O—($C_{1-6}$ alkyl), $C_{1-6}$ haloalkyl, —O—($C_{1-6}$ haloalkyl), —Si—($C_{1-6}$ alkyl)$_3$, and —O—Si($C_{1-6}$ alkyl)$_3$. In some even further embodiments of any of the aforementioned embodiments, -$G^7$-$R^{17}$ is $C_{1-12}$ alkyl, which is optionally substituted one or more times with substituents selected independently from the group consisting of a halogen atom and phenyl. In some further such embodiments of any of the aforementioned embodiments, -$G^7$-$R^{17}$ is tert-butyl, —$C(CH_3)_2(CF_3)$, —$C(CF_3)_3$, or —$C(CF_3)_2$-(phenyl).

In some other embodiments of any of the aforementioned embodiments, $R^7$ is $C_{6-20}$ aryl or $C_{2-20}$ heteroaryl, each of which is optionally substituted one or more times with substituents selected independently from $R^{31}$, wherein any two adjacent $R^{31}$ optionally combine to form a ring, which is optionally substituted one or more times with substituents selected independently from $R^x$. In some further such embodiments of any of the aforementioned embodiments, $R^7$ is phenyl, 1-naphthyl, or 2-naphthyl, each of which is optionally substituted one or more times with substituents selected independently from the group consisting of a halogen atom, $C_{1-6}$ alkyl, $C_{2-6}$ alkenyl, $C_{3-10}$ cycloalkyl, phenyl, 1-naphthyl, 2-naphthyl, —CN, —O($C_{1-6}$ alkyl), —Si($C_{1-6}$ alkyl)$_3$, and —O—Si($C_{1-6}$ alkyl)$_3$, or any two adjacent substituents can optionally combine to form a —(CH$_2$)$_3$— ring or a —(CH)$_4$— ring, wherein the cycloalkyl, phenyl, and naphthyl substituents are optionally substituted one or more times by substituents selected independently from the group consisting of a halogen atom, $C_{1-6}$ alkyl, $C_{3-10}$ cycloalkyl, phenyl, —CN, —O($C_{1-6}$ alkyl), —Si($C_{1-6}$ alkyl)$_3$, and —O—Si($C_{1-6}$ alkyl)$_3$, or any two adjacent substituents can optionally combine to form a —(CH$_2$)$_3$— ring or a —(CH)$_4$— ring. In some further embodiments of any of the aforementioned embodiments, $R^7$ is phenyl or 1-naphthyl, which is optionally substituted one or more times with substituents selected independently from the group consisting of a halogen atom, $C_{1-6}$ alkyl, phenyl, 1-naphthyl, —O($C_{1-6}$ alkyl), and —O—Si($C_{1-6}$ alkyl)$_3$, or any two adjacent alkyl substituents can optionally combine to form a —(CH$_2$)$_4$— ring, wherein the phenyl and naphthyl substituents are optionally substituted one or more times by substituents selected independently from the group consisting of a halogen atom, $C_{1-6}$ alkyl, phenyl, —O($C_{1-6}$ alkyl), and —O—Si($C_{1-6}$ alkyl)$_3$, or any two adjacent alkyl substituents can optionally combine to form a —(CH$_2$)$_4$— ring.

In some further embodiments of any of the aforementioned embodiments, $R^7$ is phenyl, which is optionally substituted one or more times by substituents selected independently from the group consisting of a halogen atom and phenyl. For example, in some such embodiments of any of the aforementioned embodiments, $R^7$ is 2,6-diphenylphenyl or 4-bromo-2,3,5,6-tetraphenylphenyl. In some further such embodiments of any of the aforementioned embodiments, $R^7$ is 2,3,5,6-tetraphenylphenyl. In some further embodiments of any of the aforementioned embodiments, $R^7$ is phenyl, which is optionally substituted one or more times by substituents selected independently from the group consisting of —$NO_2$ ("nitro") and phenyl. For example, in some such embodiments of any of the aforementioned embodiments, $R^7$ is 4-nitro-2,3,5,6-tetraphenylphenyl. In some other embodiments of any of the aforementioned embodiments, $R^7$ is phenyl or naphthyl (e.g., 1-naphthyl), which are optionally substituted by one or more times by substituents selected independently from the group consisting of a halogen atom (e.g., fluoro, chloro, or bromo), $C_{1-6}$ alkyl (e.g., methyl, ethyl, isopropyl, tert-butyl, etc.), $C_{6-20}$ aryl (e.g., phenyl, naphthyl, etc.), —O—($C_{1-6}$ alkyl) (e.g., methoxy), and —O—Si($C_{1-6}$ alkyl)$_3$ (e.g., tert-butyldimethylsilyloxy), with any two adjacent alkyl substituents optionally combining to form a —(CH$_2$)$_4$— ring, where the aryl groups are optionally further substituted one or more times by substituents selected independently from the group consisting of a halogen atom (e.g., fluoro, chloro, or bromo), $C_{1-6}$ alkyl (e.g., methyl, ethyl, isopropyl, tert-butyl, etc.), $C_{6-20}$ aryl (e.g., phenyl, naphthyl, etc.), —O—($C_{1-6}$ alkyl) (e.g., methoxy), and —O—Si($C_{1-6}$ alkyl)$_3$ (e.g., tert-butyldimethylsilyloxy). In some embodiments of any of the aforementioned embodiments, $R^7$ is

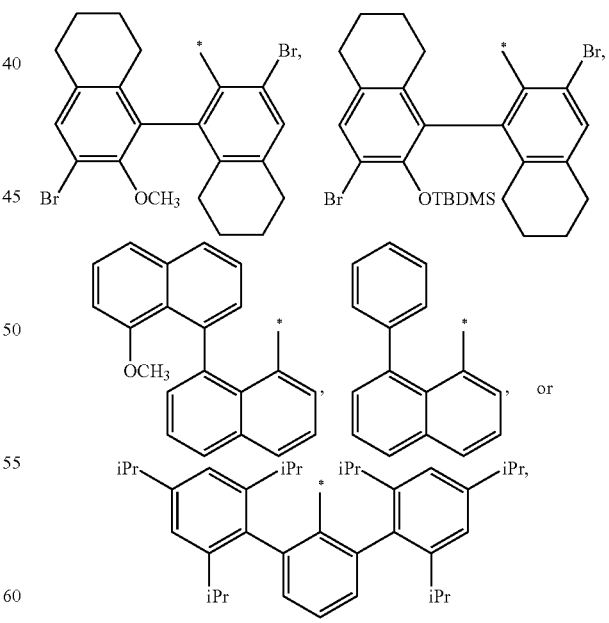

wherein "iPr" refers to isopropyl, and "OTBDMS" refers to tert-butyldimethylsilyloxy.

In some further embodiments of any of the aforementioned embodiments, $R^7$ is —$SiR^{21}R^{22}R^{23}$. In some embodiments of any of the aforementioned embodiments, $R^7$ is —Si—(C$_{1-6}$ alkyl)$_p$(phenyl)$_q$, wherein p+q=3 and p and q can each be 0, 1, 2, or 3. In some embodiments of any of the aforementioned embodiments, R$^7$ is —Si(phenyl)$_3$.

In some further embodiments of any of the aforementioned embodiments, R$^7$ is —CR$^{21}$R$^{22}$R$^{23}$. In some embodiments of any of the aforementioned embodiments, R$^7$ is —C—(C$_{1-6}$ alkyl)$_3$, wherein the alkyl groups are optionally substituted one or more times with a halogen atom (e.g., a fluorine atom). In some embodiments of any of the aforementioned embodiments, R$^7$ is —C(CH$_3$)(CF$_3$)$_2$, —C(CH$_3$)$_2$(CF$_3$), —C(CF$_3$)$_3$. In some further embodiments of any of the aforementioned embodiments, R$^7$ is —C(CH$_3$)(CF$_3$)$_2$.

In some other embodiments of any of the aforementioned embodiments, R$^{7'}$ is a hydrogen atom. In some other embodiments of any of the aforementioned embodiments, R$^{7'}$ is C$_{6-20}$ aryl or C$_{2-20}$ heteroaryl, each of which is optionally substituted one or more times with substituents selected independently from R$^{31}$, wherein any two adjacent R$^{31}$ optionally combine to form a ring, which is optionally substituted one or more times with substituents selected independently from R$^x$. In some further such embodiments of any of the aforementioned embodiments, R$^{7'}$ is phenyl, 1-naphthyl, or 2-naphthyl, each of which is optionally substituted one or more times with substituents selected independently from the group consisting of a halogen atom, C$_{1-6}$ alkyl, C$_{2-6}$ alkenyl, C$_{3-10}$ cycloalkyl, phenyl, 1-naphthyl, 2-naphthyl, —CN, —O(C$_{1-6}$ alkyl), —Si(C$_{1-6}$ alkyl)$_3$, and —O—Si(C$_{1-6}$ alkyl)$_3$, or any two adjacent substituents can optionally combine to form a —(CH$_2$)$_3$— ring or a —(CH)$_4$— ring, wherein the cycloalkyl, phenyl, and naphthyl substituents are optionally substituted one or more times by substituents selected independently from the group consisting of a halogen atom, C$_{1-6}$ alkyl, C$_{3-10}$ cycloalkyl, phenyl, —CN, —O(C$_{1-6}$ alkyl), —Si(C$_{1-6}$ alkyl)$_3$, and —O—Si(C$_{1-6}$ alkyl)$_3$, or any two adjacent substituents can optionally combine to form a —(CH$_2$)$_3$— ring or a —(CH)$_4$— ring. In some further embodiments of any of the aforementioned embodiments, R$^{7'}$ is phenyl or 1-naphthyl, which is optionally substituted one or more times with substituents selected independently from the group consisting of a halogen atom, C$_{1-6}$ alkyl, phenyl, 1-naphthyl, —O(C$_{1-6}$ alkyl), and —O—Si(C$_{1-6}$ alkyl)$_3$, or any two adjacent alkyl substituents can optionally combine to form a —(CH$_2$)$_4$— ring, wherein the phenyl and naphthyl substituents are optionally substituted one or more times by substituents selected independently from the group consisting of a halogen atom, C$_{1-6}$ alkyl, phenyl, —O(C$_{1-6}$ alkyl), and —O—Si(C$_{1-6}$ alkyl)$_3$, or any two adjacent alkyl substituents can optionally combine to form a —(CH$_2$)$_4$— ring.

In some further embodiments of any of the aforementioned embodiments, R$^{7'}$ is phenyl, which is optionally substituted one or more times by substituents selected independently from the group consisting of a halogen atom and phenyl. For example, in some such embodiments of any of the aforementioned embodiments, R$^{7'}$ is 2,6-diphenylphenyl or 4-bromo-2,3,5,6-tetraphenylphenyl. In some further such embodiments of any of the aforementioned embodiments, R$^{7'}$ is 2,3,5,6-tetraphenylphenyl. In some further embodiments of any of the aforementioned embodiments, R$^{7'}$ is phenyl, which is optionally substituted one or more times by substituents selected independently from the group consisting of —NO$_2$ ("nitro") and phenyl. For example, in some such embodiments of any of the aforementioned embodiments, R$^{7'}$ is 4-nitro-2,3,5,6-tetraphenylphenyl. In some other embodiments of any of the aforementioned embodiments, R$^7$ is phenyl or naphthyl (e.g., 1-naphthyl), which are optionally substituted by one or more times by substituents selected independently from the group consisting of a halogen atom (e.g., fluoro, chloro, or bromo), C$_{1-6}$ alkyl (e.g., methyl, ethyl, isopropyl, tert-butyl, etc.), C$_{6-20}$ aryl (e.g., phenyl, naphthyl, etc.), —O—(C$_{1-6}$ alkyl) (e.g., methoxy), and —O—Si(C$_{1-6}$ alkyl)$_3$ (e.g., tert-butyldimethylsilyloxy), with any two adjacent alkyl substituents optionally combining to form a —(CH$_2$)$_4$— ring, where the aryl groups are optionally further substituted one or more times by substituents selected independently from the group consisting of a halogen atom (e.g., fluoro, chloro, or bromo), C$_{1-6}$ alkyl (e.g., methyl, ethyl, isopropyl, tert-butyl, etc.), C$_{6-20}$ aryl (e.g., phenyl, naphthyl, etc.), —O—(C$_{1-6}$ alkyl) (e.g., methoxy), and —O—Si(C$_{1-6}$ alkyl)$_3$ (e.g., tert-butyldimethylsilyloxy). In some embodiments of any of the aforementioned embodiments, R$^{7'}$ is:

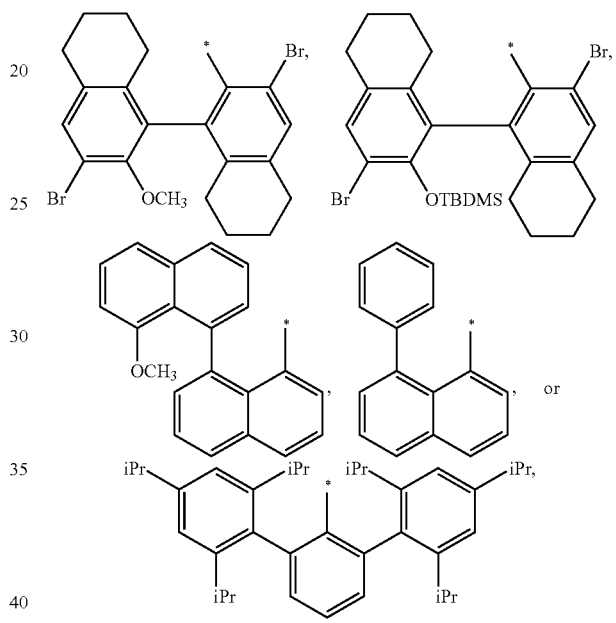

wherein "iPr" refers to isopropyl, and "OTBDMS" refers to tert-butyldimethylsilyloxy.

In some further embodiments of any of the aforementioned embodiments, R$^{7'}$ is —SiR$^{21}$R$^{22}$R$^{23}$. In some embodiments of any of the aforementioned embodiments, R$^7$ is —Si—(C$_{1-6}$ alkyl)$_p$(phenyl)$_q$, wherein p+q=3 and p and q can each be 0, 1, 2, or 3. In some embodiments of any of the aforementioned embodiments, R$^{7'}$ is —Si(phenyl)$_3$.

In some further embodiments of any of the aforementioned embodiments, R$^{7'}$ is —CR$^{21}$R$^{22}$R$^{23}$. In some embodiments of any of the aforementioned embodiments, R$^{7'}$ is —C—(C$_{1-6}$ alkyl)$_3$, wherein the alkyl groups are optionally substituted one or more times with a halogen atom (e.g., a fluorine atom). In some embodiments of any of the aforementioned embodiments, R$^{7'}$ is —C(CH$_3$)(CF$_3$)$_2$, —C(CH$_3$)$_2$(CF$_3$), —C(CF$_3$)$_3$. In some further embodiments of any of the aforementioned embodiments, R$^{7'}$ is —C(CH$_3$)(CF$_3$)$_2$.

In some further embodiments of any of the aforementioned embodiments, R$^4$ is —O—SiR$^{21}$R$^{22}$R$^{23}$. In some embodiments of any of the aforementioned embodiments, R$^4$ is —O—Si—(C$_{1-6}$ alkyl)$_r$(phenyl)$_s$, wherein r+s=3 and r and s are each 0, 1, 2, or 3, and wherein the alkyl and phenyl groups are each optionally substituted one or more times by a halogen atom (e.g., a fluorine atom). In some such embodiments of any of the aforementioned embodiments, R$^4$ is —O—Si(phenyl)$_3$.

In some further embodiments of any of the aforementioned embodiments, $R^4$ is —O—$CR^{21}R^{22}R^{23}$. In some such embodiments of any of the aforementioned embodiments, $R^4$ is —O—C—($C_{1-6}$ alkyl)$_v$(phenyl)$_w$, wherein v+w=3 and v and w are each 0, 1, 2, or 3, and wherein the alkyl and phenyl groups are each optionally substituted one or more times by a substituents selected from a halogen atom (e.g., a fluorine atom) and —O—($C_{1-6}$ alkyl). In some such embodiments of any of the aforementioned embodiments, $R^4$ is —O—C—($C_{1-6}$ alkyl)$_v$(phenyl)$_w$, wherein v+w=3 and v and w are each 0, 1, 2, or 3, and wherein the alkyl and phenyl groups are each optionally substituted one or more times by a halogen atom (e.g., a fluorine atom). In some embodiments of any of the aforementioned embodiments, $R^4$ is —O—$C(CH_3)_2(CH_2$—O—$CH_3)$. In some embodiments of any of the aforementioned embodiments, $R^4$ is —O—$C(CF_3)_2(CH_3)$.

In some further embodiments of any of the aforementioned embodiments, $R^4$ is pyrrol-1-yl, pyrazol-1-yl, imidazol-1-yl, 1H-1,2,3-triazol-1-yl, 2H-1,2,3-triazol-2-yl, 1H-1,2,4-triazol-1-yl, 4H-1,2,4-triazol-4-yl, indol-1-yl, indazol-1-yl, or azaindol-1-yl, each of which is optionally substituted one or more times with substituents selected independently from $R^8$, wherein any two adjacent $R^8$ optionally combine to form a ring, which is optionally substituted one or more times with substituents selected independently from $R^x$. In some further embodiments of any of the aforementioned embodiments, $R^4$ is pyrrol-1-yl, pyrazol-1-yl, imidazol-1-yl, 1H-1,2,3-triazol-1-yl, 2H-1,2,3-triazol-2-yl, 1H-1,2,4-triazol-1-yl, or 4H-1,2,4-triazol-4-yl, each of which is optionally substituted one or more times with substituents selected independently from $R^8$, wherein any two adjacent $R^8$ optionally combine to form a ring, which is optionally substituted one or more times with substituents selected independently from $R^x$. In some embodiments of any of the aforementioned embodiments, $R^4$ is pyrrol-1-yl or imidazol-1-yl, each of which is optionally substituted one or more times with substituents selected independently from $R^8$, wherein any two adjacent $R^8$ optionally combine to form a ring, which is optionally substituted one or more times with substituents selected independently from $R^x$. In some further embodiments of any of the aforementioned embodiments, $R^4$ is pyrrol-1-yl or imidazol-1-yl, each of which is optionally substituted one or more times with substituents selected independently from the group consisting of a $C_{1-6}$ alkyl, $C_{2-6}$ alkenyl, and phenyl, or any two adjacent substituents can optionally combine to form a —$(CH)_4$— ring. In some further embodiments of any of the aforementioned embodiments, $R^4$ is pyrrol-1-yl, which is optionally substituted (e.g., at the 2 and 5 positions) with one or more substituents selected independently from the group consisting of $C_{1-6}$ alkyl (e.g., methyl) and phenyl. In some further embodiments of any of the aforementioned embodiments, $R^4$ is imidazol-1-yl, which is optionally substituted (e.g., at the 2 and 5 positions) with one or more substituents selected independently from the group consisting of $C_{1-6}$ alkyl (e.g., methyl) and phenyl. In some further embodiments of any of the aforementioned embodiments, $R^4$ is indol-1-yl, which is optionally substituted (e.g., at the 2 position) with one or more substituents selected independently from the group consisting of $C_{1-6}$ alkyl (e.g., methyl) and phenyl. In some further embodiments of any of the aforementioned embodiments, $R^4$ is indol-1-yl, which is optionally substituted (e.g., at the 2 position) with —O—$C_{1-6}$ alkyl (e.g., —O—$CH_3$). In some embodiments of any of the aforementioned embodiments, $R^4$ is pyrrol-1-yl, 2,5-dimethylpyrrol-1-yl, 2,5-diphenylpyrrol-1-yl, 2,5-dimethylimidazol-1-yl, or indol-1-yl.

In any of the above aspects and embodiments, the compounds can include one or more stereocenters, and may undergo isomerization (e.g., syn-anti isomerization). The disclosure covers any such stereoisomers and other isomers.

In one or more further aspects, the disclosure provides compounds of Formula (II)

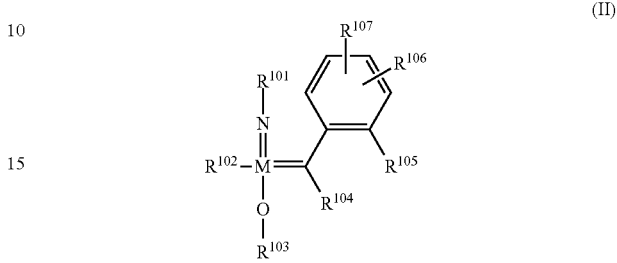

(II)

wherein:

M is a molybdenum atom or a tungsten atom;

$R^{101}$ is aryl, heteroaryl, alkyl, or cycloalkyl, each of which is optionally substituted;

$R^{102}$ is pyrrolyl, imidazolyl, indolyl, pyrazolyl, azaindolyl, or indazolyl, each of which is optionally substituted; or $R^{102}$ is —O—Si(phenyl)$_3$ when $R^{103}$ is —Si(phenyl)$_3$, the phenyl groups being optionally substituted;

$R^{103}$ is $C_{1-6}$ alkyl, $C_{1-6}$ heteroalkyl, aryl, or heteroaryl, each of which is optionally substituted; or $R^{103}$ is tert-butyl, —$C(CH_3)_2(CF_3)$, —$C(CF_3)_3$, or —$C(CF_3)_2$-(phenyl); or $R^{103}$ is —Si(phenyl)$_3$ when $R^{102}$ is —O—Si(phenyl)$_3$, the phenyl groups being optionally substituted;

$R^{104}$ is a hydrogen atom, $C_{1-6}$ alkyl, or alkoxy;

$R^{105}$ is a hydrogen atom, —O—($C_{1-6}$ alkyl), —$CH_2$—O—($C_{1-6}$ alkyl), heteroalkoxy, or —N($C_{1-6}$ alkyl)$_2$;

$R^{106}$ and $R^{107}$ are independently a hydrogen atom, $C_{1-6}$ alkyl, $C_{1-6}$ alkoxy, a halogen atom, —$NO_2$, amides, or sulfonamides.

In some further embodiments of any of the aforementioned aspects and embodiments, $R^{101}$ is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

In some further embodiments of any of the aforementioned aspects and embodiments, $R^{102}$ is pyrrolyl, imidazolyl, or indolyl, each of which is optionally substituted. In some further embodiments, $R^{102}$ is pyrrol-1-yl, 2,5-dimethylpyrrol-1-yl, 2,5-diphenylpyrrol-1-yl, 2,5-dimethylimidazol-1-yl, or indol-1-yl.

In some further embodiments of any of the aforementioned aspects and embodiments, $R^{103}$ is 2,6-diphenylphenyl, 4-bromo-2,3,5,6-tetraphenylphenyl, tert-butyl, —$C(CH_3)_2CF_3$, $C(CF_3)_3$, or —$C(CF_3)_2$(phenyl). In some other embodiments $R^{103}$ is:

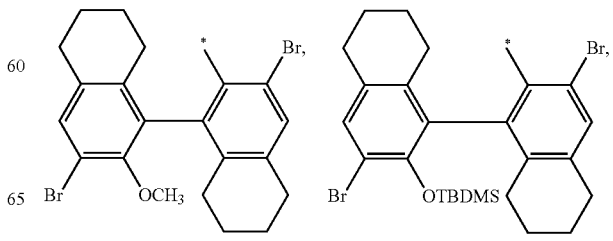

-continued

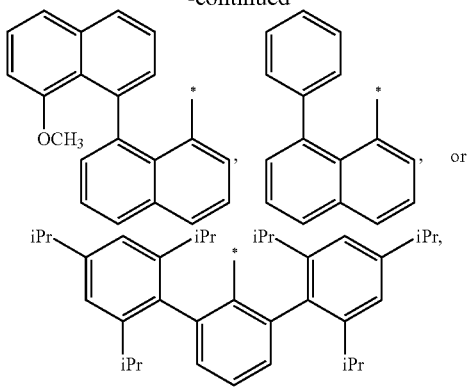

wherein "iPr" refers to isopropyl, and "OTBDMS" refers to tert-butyldimethylsilyloxy.

In some further embodiments of any of the aforementioned aspects and embodiments, $R^{104}$ is a hydrogen atom.

In some further embodiments of any of the aforementioned aspects and embodiments, $R^{105}$ is a hydrogen atom, methyloxy, ethyloxy, methyloxymethyloxy, isopropyloxy, or dimethylamino.

In some further embodiments of any of the aforementioned aspects and embodiments, $R^{106}$ and $R^{107}$ are independently a hydrogen atom, $C_{1-6}$ alkyl, $C_{1-6}$ alkoxy, or a halogen atom. In some further embodiments, $R^{106}$ and $R^{107}$ are independently a hydrogen atom, methyl, a halogen atom, or methyloxy.

In any of the above aspects and embodiments, the compounds can include one or more stereocenters, and may undergo isomerization (e.g., syn-anti isomerization). The disclosure covers any such stereoisomers and other isomers.

In some further aspects, compounds of any of the aforementioned aspects and embodiments can be illustrated by reference to specific compounds. Table 2 below provides a list of 62 compounds that illustrate compounds that are encompassed by one or more of the aforementioned aspects and embodiments. The compounds of Table 2 can be understood in terms of the generic structure of Formula (III) and the definitions of Tables 1A-1D.

TABLE 1A

| Chemical Moiety | Moiety Number |
| --- | --- |
| 2,6-Dimethylphenyl | A-1 |
| 2,6-Diisopropylphenyl | A-2 |
| 2,6-Dichlorophenyl | A-3 |
| 1-Adamantyl | A-4 |
| Pentafluorophenyl | A-5 |

TABLE 1B

| Chemical Moiety | Moiety Number |
| --- | --- |
| Pyrrol-1-yl | B-1 |
| 2,5-Dimethylpyrrol-1-yl | B-2 |
| Triphenylsilyloxy | B-3 |
| —O—C(CF$_3$)$_3$ | B-4 |
| —O—C(CH$_3$)(CF$_3$)$_2$ | B-5 |
| —O—C(CH$_3$)$_2$(CF$_3$) | B-6 |
| 2-Ethoxy-indol-1-yl | B-7 |
| —O—C(CH$_3$)$_2$—CH$_2$—O—CH$_3$ | B-8 |

TABLE 1C

| Chemical Moiety | Moiety Number |
| --- | --- |
| 2,6-Diphenylphenyl | C-1 |
| 4-Bromo-2,3,5,6-tetraphenylphenyl | C-2 |
| Triphenylsilyl | C-3 |
| (structure) | C-4 |
| (structure) | C-5 |
| (structure) | C-6 |
| +GET,347 | C-7 |
| 4-Nitro-2,3,5,6-tetraphenylphenyl | C-8 |
| —C(CH$_3$)(CF$_3$)$_2$ | C-9 |
| 2,3,5,6-Tetraphenylphenyl | C-10 |

In the above table, "OTBDMS" is tert-butyldimethylsilyloxy.

TABLE 1D

| Chemical Moiety | Moiety Number |
| --- | --- |
| 2-Methoxyphenyl | D-1 |
| 4-Fluoro-2-methoxyphenyl | D-2 |
| 5-Fluoro-2-methoxyphenyl | D-3 |
| 2,4-Dimethoxyphenyl | D-4 |
| 2,5-Dimethoxyphenyl | D-5 |
| 2-Methoxy-4-methylphenyl | D-6 |
| 2-Methoxy-5-methylphenyl | D-7 |
| Phenyl | D-8 |
| 2,4,5-Trimethoxyphenyl | D-9 |
| 2-Ethoxyphenyl | D-10 |
| 2-Isopropoxyphenyl | D-11 |
| 2-(Methoxymethyl)phenyl | D-12 |
| 2-(Dimethylamino)phenyl | D-13 |
| 2-Pyridyl (i.e., Pyridin-2-yl) | D-14 |
| —O-(tetrahydropyran-2-yl) | D-15 |
| —O—(C=O)—CH$_3$ | D-16 |
| —O—(C=O)—C(CH$_3$)$_3$ | D-17 |
| —O—(C=O)-(phenyl) | D-18 |
| 2-Methoxy-4-nitrophenyl | D-19 |
| Pyrrolidin-2-on-1-yl | D-20 |
| 2-Methoxy-pyridin-3-yl | D-21 |

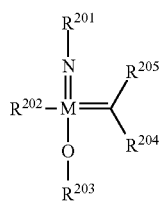

(III)

TABLE 2

| Compound | M | R²⁰¹ | R²⁰² | R²⁰³ | R²⁰⁴ | R²⁰⁵ |
|---|---|---|---|---|---|---|
| 1 | Mo | A-1 | B-2 | C-1 | H | D-1 |
| 2 | W | A-3 | B-2 | C-4 | H | D-1 |
| 3 | W | A-3 | B-2 | C-2 | H | D-1 |
| 4 | Mo | A-2 | B-2 | C-2 | H | D-1 |
| 5 | W | A-3 | B-2 | C-4 | H | D-2 |
| 6 | W | A-3 | B-2 | C-4 | H | D-3 |
| 7 | W | A-3 | B-2 | C-6 | H | D-1 |
| 8 | W | A-3 | B-2 | C-4 | H | D-5 |
| 9 | W | A-3 | B-2 | C-4 | H | D-4 |
| 10 | W | A-3 | B-2 | C-4 | H | D-8 |
| 11 | W | A-3 | B-2 | C-4 | H | D-6 |
| 12 | W | A-3 | B-2 | C-4 | H | D-7 |
| 13 | W | A-3 | B-2 | C-4 | H | D-9 |
| 14 | W | A-3 | B-2 | C-7 | H | D-1 |
| 15 | W | A-3 | B-2 | C-4 | H | D-10 |
| 16 | W | A-3 | B-2 | C-4 | H | D-11 |
| 17 | W | A-3 | B-2 | C-4 | H | D-12 |
| 18 | Mo | A-1 | B-2 | C-4 | H | D-1 |
| 19 | Mo | A-2 | B-2 | C-4 | H | D-1 |
| 20 | W | A-3 | B-2 | C-4 | H | D-13 |
| 21 | Mo | A-2 | B-2 | C-1 | H | D-1 |
| 22 | W | A-3 | B-2 | C-5 | H | D-1 |
| 23 | Mo | A-4 | B-2 | C-4 | H | D-1 |
| 24 | Mo | A-4 | B-2 | C-5 | H | D-1 |
| 25 | Mo | A-1 | B-2 | C-5 | H | D-1 |
| 26 | Mo | A-2 | B-2 | C-5 | H | D-1 |
| 27 | W | A-1 | B-2 | C-4 | H | D-1 |
| 28 | W | A-3 | B-2 | C-2 | H | D-2 |
| 29 | W | A-3 | B-2 | C-2 | H | D-4 |
| 30 | W | A-3 | B-2 | C-2 | H | D-6 |
| 31 | W | A-3 | B-2 | C-2 | H | D-12 |
| 32 | W | A-3 | B-2 | C-2 | H | D-13 |
| 33 | Mo | A-2 | B-3 | C-3 | H | D-1 |
| 34 | W | A-2 | B-3 | C-3 | H | D-1 |
| 35 | W | A-3 | B-2 | C-2 | H | D-14 |
| 36 | Mo | A-2 | B-2 | C-2 | H | D-14 |
| 37 | Mo | A-2 | B-5 | C-2 | H | D-1 |
| 38 | Mo | A-2 | B-4 | C-2 | H | D-1 |
| 39 | Mo | A-2 | B-6 | C-2 | H | D-1 |
| 40 | Mo | A-2 | B-2 | C-2 | H | D-15 |
| 41 | Mo | A-2 | B-7 | C-2 | H | D-1 |
| 42 | W | A-3 | B-6 | C-2 | H | D-1 |
| 43 | W | A-3 | B-5 | C-2 | H | D-1 |
| 44 | W | A-3 | B-4 | C-2 | H | D-1 |
| 45 | Mo | A-2 | B-2 | C-4 | H | D-15 |
| 46 | W | A-2 | B-7 | C-2 | H | D-1 |
| 47 | Mo | A-2 | B-7 | C-9 | H | D-1 |
| 48 | W | A-3 | B-8 | C-2 | H | D-1 |
| 49 | W | A-3 | B-7 | C-2 | H | D-1 |
| 50 | Mo | A-2 | B-2 | C-2 | H | D-16 |
| 51 | W | A-2 | B-2 | C-2 | H | D-1 |
| 52 | Mo | A-2 | B-2 | C-2 | H | D-17 |
| 53 | W | A-5 | B-2 | C-4 | H | D-1 |
| 54 | Mo | A-2 | B-2 | C-2 | H | D-18 |
| 55 | Mo | A-2 | B-2 | C-2 | H | D-19 |
| 56 | W | A-3 | B-2 | C-2 | H | D-19 |
| 57 | Mo | A-2 | B-2 | C-8 | H | D-1 |
| 58 | W | A-3 | B-2 | C-8 | H | D-1 |
| 59 | W | A-3 | B-2 | C-10 | H | D-1 |
| 60 | Mo | A-2 | B-2 | C-2 | H | D-15 |
| 61 | Mo | A-2 | B-2 | C-2 | H | D-20 |
| 62 | W | A-3 | B-2 | C-2 | H | D-20 |
| 63 | Mo | A-2 | B-2 | C-2 | H | D-21 |
| 64 | W | A-3 | B-2 | C-2 | H | D-21 |

Compound Preparation

The compounds disclosed in any of the aforementioned aspects and embodiments, including the compounds in Table 2, may be prepared by methods known in the art using commercially available materials and art-recognized methods. Illustrative synthetic methods are recited below in the Examples. The ordinarily skilled artisan may use these examples as a guide and thereby prepare other compounds in an analogous manner using ordinary skill in the art.

Methods of Use

The compounds disclosed in any of the aforementioned aspects and embodiments, including the compounds in Table 2, may be used to catalyze olefin metathesis reactions of various kinds. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be catalyzed by the compounds disclosed herein. Therefore, the compounds disclosed herein can be suitable used for making various compounds that may otherwise be difficult to make, including, but not limited to, pharmaceutical compounds, agrochemical compounds, flavor compounds, and fragrance compounds.

In certain aspects, the disclosure provides methods of carrying out a metathesis reaction, including: providing a first compound having one or more carbon-carbon double bonds; and reacting the first compound via a metathesis reaction in the presence of a metathesis catalyst, such as a compound of any of the aforementioned aspects and embodiments.

In some embodiments, the first compound has two or more carbon-carbon double bonds. In some such embodiments, the metathesis reaction is a ring-closing metathesis reaction between two of the two or more carbon-carbon double bonds of the first compound. In some such embodiments, a catalytically effective amount of the metathesis catalyst is present. The catalytically effective amount can vary depending on the nature of the reaction being catalyzed and the desired product.

In some other aspects, the disclosure provides methods of carrying out a metathesis reaction, including: providing a first compound having one or more carbon-carbon double bond and a second compound having one or more carbon-carbon double bonds; and reacting the first compound and the second compound via a metathesis reaction in the presence of a metathesis catalyst, such as a compound of the first or second aspects disclosed herein.

In some embodiments, the first compound and the second compound are the same compound, meaning that the reaction is a self-metathesis reaction. In some other embodiments, the first compound and the second compound are not the same, meaning that it is a cross-metathesis reaction.

In some such embodiments, the first compound is an internal olefin, such as a natural oil. In some embodiments, the second compound is a short-chain alkene, such as ethylene. In some such embodiments, the metathesis reaction yields an amount of 9-decenoic acid or an ester or carboxylate salt thereof.

Any suitable catalyst loadings can be used for the metathesis reactions. For example, in some embodiments, the catalyst loading relative to the metathesis substrate (e.g., a natural oil triglyceride) is no more than 2000 molar ppm, or no more than 1500 molar ppm, or no more than 1000 molar ppm, or no more than 500 molar ppm, or no more than 350 molar ppm, or no more than 200 molar ppm, or no more than 175 molar ppm, or no more than 140 molar ppm, or no more than 100 molar ppm, or no more than 70 molar ppm. In some embodiments, the catalyst loading relative to the metathesis substrate (e.g., a natural oil triglyceride) is from 15 to 2000 molar ppm, or from 15 to 1000 molar ppm, or from 25 to 500 molar ppm, or from 35 to 350 molar ppm, or from 35 to 200 molar ppm, or from 35 to 175 molar ppm, or from 35 to 200 molar ppm.

Metathesis of Natural Oils

In some embodiments, the compounds disclosed in the aforementioned aspects and embodiments can be suitable used to metathesize natural oils, e.g., as glycerides, as alkyl esters (e.g., methyl esters), etc. Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst (such as those disclosed herein), some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275681, and 2014/0275595, all three of which are hereby incorporated by reference as though fully set forth herein.

For example, in some embodiments, the metathesis substrate materials to be subjected to metathesis reactions using the compounds disclosed herein are purified from impurities that may poison the catalytic effect of the compounds. Suitable methods include, but are not limited to, percolation through molecular sieves to remove water (or reduce water content to the acceptable level), optionally followed by a further percolation through activated alumina to remove/cleave organic peroxide and eliminate other impurities (e.g. alcohols, aldehydes, ketones). In some embodiments, distillation from sodium and/or potassium (e.g. styrene) may be sufficient to obtain suitably pure substrates. Similarly, when the water content is not high (e.g., less than about 250 ppm, relative to the concentration of the metathesis substrate material), percolation through alumina may be sufficient. A typical commercially-available alumina is SELEXSORB (BASF, Leverkusen, Germany). This is an activated alumina-based adsorbent containing a proprietary modifier, and is used as an industrial adsorbent.

In some other embodiments, olefin feedstocks are used without purification, e.g., if trialkylaluminum (e.g. triethylaluminum) is added to the metathesis reaction. In such instances, trialkylaluminum may be used as an additive, e.g., in an amount of 0.5-5.0 mol %, relative to the concentration of the metathesis substrate material. Using this method or a combination of trialkylaluminum with molecular sieves and/or alumina may provide <10 ppm water content and, in some cases, the peroxide content is reduced, e.g., to below its detection limit.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

For example, multiple metathesis can be employed to make the dibasic acid compounds used to make the diesters disclosed herein. In some embodiments, alkyl (e.g., methyl) esters of 9-decenoic acid, 9-undecenoic acid, 9-dodecenoic acid, or any combination thereof, can be reacted in a self-metathesis reaction or a cross-metathesis to generate various unsaturated dibasic alkyl esters, such as dimethyl 9-octadecendioate. Such compounds can then be converted to dibasic acids by hydrolysis or via saponification followed by acidification. If a saturated dibasic acid is desired, the compound can be hydrogenated, either before conversion to the acid or after. Dibasic acids of other chain lengths can be made by analogous means. The conditions for such metathesis reactions, and the reactor design, and suitable catalysts are as described below with reference to the metathesis of the olefin esters. That discussion is incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used. In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The reactor design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

In certain embodiments, the metathesis catalyst (such as the compounds disclosed herein) is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

EXAMPLES

General Procedures

The following general procedures were used to make the compounds disclosed in Table 2. All complexes were handled in a glovebox under a nitrogen ($N_2$) atmosphere. Benzene and 1,2-dimethoxyethane were distilled from sodium or potassium and stored on activated molecular sieves in a nitrogen-filled glovebox. Then, n-Pentane was washed with sulfuric acid, followed by water and saturated aqueous solution of sodium hydrogencarbonate, dried over calcium chloride pellets, and distilled from potassium. Benzene-$d_6$ was dried over activated molecular sieves.

All $^1$H-NMR spectra were recorded using a Varian Mercury (200 MHz) or Bruker Avance (300 MHz) spectrometer. Chemical shifts were reported in ppm from tetramethylsilane with the solvent resonance resulting from incomplete deuteration as the internal reference ($C_6D_6$: δ 7.16, $CDCl_3$: δ 7.24). Data were reported as follows: chemical shift, integration, multiplicity (s=singlet, d=doublet, t=triplet, br=broad, m=multiplet), coupling constants (Hz). GC spectra were performed on a Shimadzu GC-2010 Plus, and MS spectra were recorded on a GCMS-QP 2010 Ultra.

The compounds were made in a manner consistent with the experimental procedures set forth in the following references: (1) T. Kreickmann et al., Organometallics, 2007, 5702-5711 (and references cited therein); (2) L. Gerber et al., Organometallics, 2013, 2373-2378; (3) R. Singh et al., Organometallics, 2007, 2528-2539; (4) U.S. Pat. No. 8,362, 311; (5) A. S. Hock et al., J. A. Chem. Soc., 2006, 16373-16375; (6) S. C. Martinescu, Organometallics, 2008, 6570-6578; (7) P. Wipf et al. J. Org. Chem., 2001, 3133-3139; (8) Bellera M. et al., Tetrahedron, 2008, 1316-1322; (9) Masa-hiro M. et al. Angew. Chem. Int. Ed., 1997, 1740-1742; and (10) D. H. Hua et al., Tetrahedron Asymmetry, 2001, 1999-2004.

In some instances, reagents used to make the catalysts were passed through activated alumina before use. For example, oct-1-ene, allylbenzene, and diethyl diallylmalonate were passed through activated alumina and stored on activated molecular sieves in a nitrogen-filled glovebox prior to use.

Synthesis of Intermediate Compounds

Intermediates used to make the compounds disclosed herein were prepared by the following procedures.

Synthesis of 4-fluoro-1-methoxy-2-vinylbenzene. A suspension of 12.73 g of methyl triphenylphosphonium bromide in 100 mL of dry THF was treated at room temperature with 15.6 mL of n-butyl lithium (n-BuLi) (2.5 M solution in n-hexane). The resulting orange solution was stirred for 4 hours. Then, a solution of 5.00 g of 5-fluoro-2-methoxybenzaldehyde in 25 mL of dry tetrahydrofuran (THF) was added dropwise. Upon addition, a white precipitate formed. The suspension was stirred for 1 hour and concentrated in vacuo to give a viscous orange oil that was purified by passing it through a short column of $SiO_2$ (heptane), then vacuum distilled to yield 525 mg of 4-fluoro-1-methoxy-2-vinylbenzene as a colorless liquid. $^1$H-NMR (300 MHz, $CDCl_3$): δ 3.75 (s, 3H), 5.23 (dd, $J_1$=11.1 Hz, $J_2$=1.5 Hz, 1H), 5.64 (dd, $J_1$=17.7 Hz, $J_2$=1.5 Hz, 1H), 6.69-6.74 (m, 1H), 6.81-6.98 (m, 1H), 7.07-7.12 (m, 1H). GC-MS: 97.0% MS (EI): 152.

Synthesis of 4-fluoro-2-methoxy-1-vinylbenzene. A suspension of 12.73 g of methyl triphenylphosphonium bromide in 100 mL of dry THF was treated at room temperature with 15.6 mL of n-BuLi (2.5 M solution in n-hexane). The resulting orange solution was stirred for 4 hours. Then, a solution of 5.00 g of 4-fluoro-o-anisaldehyde in 25 mL of dry THF was added dropwise. Upon addition a white precipitate formed. The suspension was stirred for 1 hour and concentrated in vacuo to give a viscous orange oil that was purified by passing through a short column of $SiO_2$ (heptane) then vacuum distillation to yield 321 mg of 4-fluoro-2-methoxy-1-vinylbenzene as a colorless liquid. $^1$H-NMR (300 MHz, $CDCl_3$): δ 3.76 (s, 3H), 5.15 (dd, $J_1$=11.1 Hz, $J_2$=1.4 Hz, 1H), 5.69 (dd, $J_1$=17.6 Hz, $J_2$=1.4 Hz, 1H), 6.48-6.60 (m, 2H), 6.81-6.94 (m, 1H), 7.29-7.37 (m, 1H). GC-MS: 97.5% MS (EI): 152.

Synthesis of 1,4-dimethoxy-2-vinylbenzene. A suspension of 11.71 g of methyl triphenylphosphonium bromide in 100 mL of dry THF was treated at room temperature with 14.3 mL of n-BuLi (2.5 M solution in n-hexane). The resulting orange solution was stirred for 4 hours. Then, a solution of 5.00 g of 2,5-dimethoxybenzaldehyde in 25 mL of dry THF was added dropwise. Upon addition, a white precipitate formed. The suspension was stirred for 1 hour and concentrated in vacuo to give a viscous orange oil that was purified by passing through a short column of $SiO_2$ (heptane) then vacuum distillation to yield 1.92 g of 1,4-dimethoxy-2-vinylbenzene as a colorless liquid. $^1$H-NMR (300 MHz, $CDCl_3$): δ 3.71 (s, 3H), 3.73 (s, 3H), 5.19 (dd, $J_1$=11.2 Hz, $J_2$=1.6 Hz, 1H), 5.64 (dd, $J_1$=17.7 Hz, $J_2$=1.6 Hz, 1H), 6.68-6.75 (m, 2H), 6.90-6.99 (m, 2H). GC-MS: 98.0% MS (EI): 164.

Synthesis of 2,4-dimethoxy-1-vinylbenzene. A suspension of 11.59 g of methyl triphenylphosphonium bromide in 100 mL of dry THF was treated at room temperature with 14.2 mL of n-BuLi (2.5 M solution in n-hexane). The resulting orange solution was stirred for 4 hour. Then, a solution of 5.00 g of 2,4-dimethoxybenzaldehyde in 25 mL of dry THF was added dropwise. Upon addition, a white precipitate formed. The suspension was stirred for 1 hour and concentrated in vacuo to give a viscous orange oil that was purified by passing through a short column of $SiO_2$ (heptane) then vacuum distillation to yield 1.96 g of 2,4-dimethoxy-1-vinylbenzene as a colorless liquid. $^1$H-NMR (300 MHz, $CDCl_3$): δ 3.74 (s, 3H), 3.75 (s, 3H), 5.06 (dd, $J_1$=11.2 Hz, $J_2$=1.5 Hz, 1H), 5.55 (dd, $J_1$=17.7 Hz, $J_2$=1.5 Hz, 1H), 6.34-6.43 (m, 2H), 6.80-6.94 (m, 1H), 7.31 (d, J=8.4 Hz, 1H). GC-MS: 95.6% MS (EI): 164.

Synthesis of 1-methoxy-4-methyl-2-vinylbenzene. A suspension of 8.68 g of methyl triphenylphosphonium bromide in 60 mL of dry THF was treated at room temperature with 10.6 mL of n-BuLi (2.5 M solution in n-hexane). The resulting orange solution was stirred for 4 hours. Then, a solution of 3.32 g of 2-methoxy-5-methyl-benzaldehyde in 25 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 765 mg of 1-methoxy-4-methyl-2-vinylbenzene as a colorless liquid. $^1$H-NMR (300 MHz, $CDCl_3$): δ 2.22 (s, 3H), 3.75 (s, 3H), 5.17 (dd, $J_1$=11.1 Hz, $J_2$=1.4 Hz, 1H), 5.64 (dd, $J_1$=17.8 Hz, $J_2$=1.4 Hz, 1H), 6.69 (d, J=8.3 Hz, 1H), 6.86-7.01 (m, 2H), 7.17 (d, J=8.0 Hz, 1H). GC-MS: 98.4% MS (EI): 148.

Synthesis of 2-methoxy-4-methyl-1-vinylbenzene. A suspension of 13.08 g of methyl triphenylphosphonium bromide in 75 mL of dry THF was treated at room temperature with 16.0 mL of n-BuLi (2.5 M solution in n-hexane). The resulting orange solution was stirred for 4 hour. Then, a solution of 5.00 g of 2-methoxy-4-methyl-benzaldehyde in 25 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 1.46 g of 2-methoxy-4-methyl-1-vinylbenzene as a colorless liquid. $^1$H-NMR (300 MHz, $CDCl_3$): δ 2.27 (s, 3H), 3.76 (s, 3H), 5.13 (dd, $J_1$=11.2 Hz, $J_2$=1.5 Hz, 1H), 5.61 (dd, $J_1$=17.7 Hz, $J_2$=1.5 Hz, 1H), 6.61 (s, 1H), 6.67 (m, 1H), 6.93 (m, 1H), 7.28 (d, J=7.7 Hz, 1H). GC-MS: 97.8% MS (EI): 148.

Synthesis of 1,2,4-trimethoxy-5-vinylbenzene. A suspension of 10.02 g of methyl triphenylphosphonium bromide in 75 mL of dry THF was treated at room temperature with 12.2 mL of n-BuLi (2.5 M solution in n-hexane). The resulting orange solution was stirred for 4 h. Then, a solution of 5.00 g (25.5 mmol) of 2,4,5-trimethoxy-benzaldehyde in 25 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 1.71 g of 1,2,4-trimethoxy-5-vinylbenzene as a colorless liquid. $^1$H-NMR (300 MHz, $CDCl_3$): δ 3.76 (s, 3H), 3.80 (s, 3H), 3.83 (s, 3H), 5.09 (dd, $J_1$=11.1 Hz, $J_2$=1.4 Hz, 1H), 5.52 (dd, $J_1$=17.7 Hz, $J_2$=1.4 Hz, 1H), 6.44 (s, 1H), 6.86-6.98 (m, 2H). GC-MS: 95.1% MS (EI): 194.

Synthesis of 1-ethoxy-2-vinylbenzene. A suspension of 14.28 g of methyl triphenylphosphonium bromide in 80 mL of dry THF was treated at room temperature with 17.3 mL of n-BuLi (2.5 M solution in n-hexane). The resulting orange solution was stirred for 4 hours. Then, a solution of 5.00 g of 2-ethoxybenzaldehyde in 25 mL of dry THF was added dropwise. Upon addition a white precipitate formed. The suspension was stirred for 1 hour and concentrated in vacuo to give a viscous yellow oil that was purified by passing through a short column of $SiO_2$ (heptane) then vacuum distillation to yield 2.86 g of 1-ethoxy-2-vinylbenzene as a colorless liquid. $^1$H-NMR (300 MHz, $CDCl_3$): δ 1.37 (t, J=7.0 Hz, 3H), 3.98 (q, J=7.0 Hz, 2H), 5.17 (dd, $J_1$=11.2 Hz, $J_2$=1.6 Hz, 1H), 5.68 (dd, $J_1$=17.8 Hz, $J_2$=1.6 Hz, 1H), 6.74-6.89 (m, 2H), 6.94-7.08 (m, 1H), 7.08-7.18 (m, 1H), 7.39 (dd, $J_1$=7.6 Hz, $J_2$=1.7 Hz, 1H). GC-MS: 98.5% MS (EI): 148.

Synthesis of 1-isopropoxy-2-vinylbenzene. A suspension of 15.65 g of methyl triphenylphosphonium bromide in 100 mL of dry THF was treated at room temperature with 19.0 mL of n-BuLi (2.5 M solution in n-hexane). The resulting orange solution was stirred for 4 hours. Then, a solution of 6.00 g (36.5 mmol) of 2-isopropoxybenzaldehyde in 25 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 3.66 g of 1-isopropoxy-2-vinylbenzene as a colorless liquid. $^1$H-NMR (300 MHz, $CDCl_3$): δ 1.27 (d, J=6.1 Hz, 6H), 4.47 (m, 1H), 5.15 (dd, $J_1$=11.2 Hz, $J_2$=1.6 Hz, 1H), 5.65 (dd, $J_1$=17.8 Hz, $J_2$=1.6 Hz, 1H), 6.78-6.88 (m, 2H), 6.92-7.05 (m, 1H), 7.08-7.16 (m, 1H), 7.40 (dd, $J_1$=7.6 Hz, $J_2$=1.7 Hz, 1H). GC-MS: >99.0% MS (EI): 162.

Synthesis of 1-(methoxymethyl)-2-vinylbenzene. A suspension of 6.62 g of methyl triphenylphosphonium bromide in 30 mL of dry THF was treated at room temperature with 8.35 mL of n-BuLi (2.5 M solution in n-hexane). The resulting orange solution was stirred for 4 hours. Then, a solution of 1.74 g of 2-(methoxymethyl)-benzaldehyde in 10 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 354 mg of 1-(methoxymethyl)-2-vinylbenzene as a colorless liquid. $^1$H-NMR (300 MHz, $CDCl_3$): δ 3.32 (s, 3H), 4.44 (s, 2H), 5.25 (dd, $J_1$=11.0 Hz, $J_2$=1.4 Hz, 1H), 5.60 (dd, $J_1$=17.4 Hz, $J_2$=1.4 Hz, 1H), 6.88-7.00 (m, 1H), 7.12-7.29 (m, 3H), 7.46 (dm, $J_1$=7.0 Hz, 1H). GC-MS: >99.0% MS (EI): 148.

Synthesis of N,N-dimethyl-2-vinylaniline. A suspension of 12.16 g of methyl triphenylphosphonium bromide in 80 mL of dry THF was treated at room temperature with 16.30 mL of n-BuLi (2.5 M solution in n-hexane). The resulting orange solution was stirred for 4 h. Then, a solution of 3.39 g (22.7 mmol) of 2-(dimethylamino)-benzaldehyde in 20 mL of dry THF was added dropwise. Upon addition, a white precipitate formed. The suspension was stirred for 1 hour and concentrated in vacuo to give a viscous yellow oil that was purified by passing through a short column of $SiO_2$ (heptane) then vacuum distillation to yield 448 mg of N,N-dimethyl-2-vinylaniline as a colorless liquid. $^1$H-NMR (300 MHz, $CDCl_3$): δ 2.65 (s, 6H), 5.17 (dd, $J_1$=11.0 Hz, $J_2$=1.6 Hz, 1H), 5.58 (dd, $J_1$=17.1 Hz, $J_2$=1.6 Hz, 1H), 6.86-7.03 (m, 3H), 7.11-7.18 (m, 1H), 7.39 (dd, $J_1$=7.5 Hz, $J_2$=1.7 Hz, 1H). GC-MS: >99.0% MS (EI): 147.

Synthesis of 2-methoxy-4-nitro-1-vinylbenzene. A suspension of 10.85 g of methyl triphenylphosphonium bromide in 100 mL of dry THF was treated at room temperature with 13.20 mL of n-BuLi (2.5 M solution in n-hexane). The resulting orange solution was stirred for 4 hours. Then, a solution of 5.00 g of 2-methoxy-4-nitrobenzaldehyde in 50 mL of dry THF was added dropwise. Upon addition, a white precipitate formed. The suspension was stirred for 1 hour and concentrated in vacuo to give a viscous yellow oil that was purified by passing it through a short column of SiO$_2$ (heptane) and then vacuum distilling to yield 666 mg of 2-methoxy-4-nitro-1-vinylbenzene as a yellow liquid. $^1$H-NMR (300 MHz, CDCl$_3$): δ 3.95 (s, 3H), 5.48 (dd, J$_1$=12.0 Hz, J$_2$=1.3 Hz, 1H), 5.90 (dd, J$_1$=16.0 Hz, J$_2$=1.4 Hz, 1H), 7.00-7.9 (m, 1H), 7.57 (d, J$_1$=8.47 Hz, 1H), 7.72 (d, J$_1$=2.15 Hz, 1H), 5.48 (dd, J$_1$=8.45 Hz, J$_2$=2.0 Hz, 1H). GC-MS: >99.0% MS (EI): 179.

Synthesis of 4-bromo-2,3,5,6-tetraphenylphenol. Under nitrogen atmosphere to the solution of dibenzyl ketone (84.95 g, 1.0 equiv.) and benzalacetophenone (84.14 g, 1.0 equiv.) in dry methanol (250-300 mL) a solution of sodium methoxide in methanol (140-150 mL) (prepared from 2.0 equiv. of sodium in 140-150 mL dry methanol) was added dropwise over 10-15 minutes at room temperature (rt), then the reaction mixture was stirred at rt for 18-20 hours under inert atmosphere. After the reaction was completed, the reaction mixture was diluted with water (450-500 mL) and the pH was adjusted to 5-6 by 37% aqueous HCl solution; the white precipitate was filtered off and washed with water. The crude product was recrystallized from methanol to deliver 2,3,5,6-tetraphenylcyclohex-2-enone (147.8 g) as an off-white solid. In a 3-necked 2-L rounded bottom flask equipped with thermometer, condenser and dropping funnel 2.3 equiv. of bromine (45.95 g, 14.73 mL) was dissolved in acetic acid (600 mL) as it was heated to 75-80° C. During this time 2,3,5,6-tetraphenyl-cyclohex-2-enone was suspended in 100 mL of acetic acid and it was added to the reaction mixture over 10-minute period. The heating was continued until HBr formation could be detected, then the reaction mixture was cooled to 40-45° C. and it was poured into water (1-1.5 L) and the yellow precipitate was filtered off, washed consecutively with water (3×250 mL), n-heptane (3×150 mL) and methanol (2×150 mL) to yield 4-bromo-2,3,5,6-tetraphenylphenol (45.72 g) as an off-white solid. $^1$H-NMR (300 MHz, CDCl$_3$): δ 4.93 (s, 1H), 6.95-7.20 (m, 20H). GC-MS: >99.0% MS (EI): 476, 478.

Synthesis of 4-nitro-2,3,5,6-tetraphenylphenol. To a solution of 4-bromo-2,3,5,6-tetraphenylphenol (1.00 g) in acetonitrile (20 mL), silver nitrite (0.48 g) was added and the reaction mixture was refluxed for 20 hours. After the completion of the reaction, the salt phase was filtered off and the organic phase was concentrated. The crude product was purified by column chromatography (Heptane:EtOAc=7:3) to yield 350 mg of 4-nitro-2,3,5,6-tetraphenylphenol as off-white solid. $^1$H-NMR (300 MHz, DMSO-d$_6$): δ 7.08-7.22 (m, 20H), 8.53 (s, 1H). GC-MS: >99.0% MS (EI): 443.

Synthesis of (R)-3,3'-dibromo-2'-(tert-butyldimethylsilyloxy)-5,5',6,6',7,7',8,8'-octahydro-1,1'-binaphthyl-2-ol. To a solution of (R)-3,3'-dibromo-5,5',6,6',7,7',8,8'-octahydro-1,1'-binaphthyl-2,2'-diol (60.0 g) and tert-butyldimethylsilyl chloride (26.1 g) in dichloromethane (400 mL) was added triethyl amine (17.5 g) dropwise and the reaction mixture was stirred at room temperature for 16 hours. After completion of the reaction it was diluted with saturated aqueous solution of ammonium chloride (ca. 100 mL), the water phase was extracted with dichloromethane twice. The combined organic phases were washed with water and brine, dried over MgSO$_4$ and evaporated. The crude product was recrystallized from methanol to yield (R)-3,3'-dibromo-2'-(tert-butyldimethylsilyloxy)-5,5',6,6',7,7',8,8'-octahydro-1,1'-binaphthyl-2-ol (68.9 g) as off-white solid. $^1$H-NMR (300 MHz, CDCl$_3$): δ−0.35 (s, 3H), 0.11 (s, 3H), 0.82 (s, 9H), 1.52-1.82 (m, 8H), 1.88-2.08 (m, 2H), 2.25-2.51 (m, 2H), 2.64-2.77 (m, 4H), 5.12 (s, 1H), 7.21 (s, 1H), 7.32 (s, 1H). GC-MS: >99.0% MS (EI): 564, 566, 568.

Synthesis of (R)-3,3'-dibromo-2'-methoxy-5,5',6,6',7,7',8,8'-octahydro-1,1'-binaphthyl-2-ol. To the solution of (R)-3,3'-dibromo-5,5',6,6',7,7',8,8'-octahydro-1,1'-binaphthyl-2,2'-diol (25.1 g) in acetonitrile (200 ml) potassium carbonate (11.5 g) and iodomethane (9.47 g, 4.15 mL) were added at room temperature and the mixture was stirred at the same temperature for 18 hours. After all starting material had been disappeared from the reaction mixture the solvent was removed in vacuo, the residue was dissolved in chloroform (150 mL) and washed with water (75 mL) and brine (75 mL), dried over MgSO$_4$ and evaporated. The crude product was purified by column chromatography to yield (R)-3,3'-dibromo-5,5',6,6',7,7',8,8'-octahydro-1,1'-binaphthyl-2,2'-diol (11.4 g, 44%) as off-white solid. $^1$H-NMR (300 MHz, CDCl$_3$): δ 1.12-1.55 (m, 8H), 1.90-2.01 (m, 2H), 2.11-2.26 (m, 6H), 3.41 (s, 3H), 4.98 (s, 1H), 7.19 (s, 1H), 7.29 (s, 1H). GC-MS: >99.0% MS (EI): 464, 466, 468.

Synthesis of potassium 2-ethoxyindol-1-ide. To a solution of 2-oxindole (1.00 g) in dichloromethane (10 mL), triethyloxonium tetrafluoroborate (1.50 g) was added to the solution and it was refluxed for 20 hours. After completion of the reaction, it was cooled to room temperature and washed with water (10 mL) and brine (10 mL), dried over MgSO$_4$ and evaporated. The crude product was recrystallized from heptane. The off-white solid was dissolved in tetrahydrofuran (10 mL) and potassium hydride was added to the reaction mixture portionwise. After the addition was completed, it was stirred at room temperature for 2 hours, then the solvent was removed in vacuo to produce 750 mg of the potassium salt.

Synthetic Preparation of Compounds Disclosed Herein.

The below examples describe the synthesis of certain compounds shown in Table 2. Every compound in Table 2 was synthesized. For those compounds for which syntheses are not reported, the compounds were synthesized in a manner analogous to the syntheses set forth below. Each example identifies the compound from Table 2 by "Compound #". Thus, "Compound 2" refers to the second compound set forth in Table 2. The descriptions below use various abbreviations, which are known to those of skill in the art, and which have the following meanings.

TBS-Bitet-2-OH refers to
2,6-Cl$_2$C$_6$H$_3$ refers to 2,6-dichlorophenyl.
CHCMe$_3$ refers to =CH—C(CH$_3$)$_3$
CHC(Me)$_2$Ph refers to =CH—C(phenyl)(CH$_3$)$_2$
NC$_4$(CH$_3$)$_2$H$_2$ refers to 2,5-dimethylpyrrolide.
4Br-TPPOH refers to 4-bromo-2,3,5,6-tetraphenylphenol.
4Br-TPPO refers to 4-bromo-2,3,5,6-tetraphenyloxide.
2,6-i-Pr$_2$C$_6$H$_3$ refers to 2,6-diisopropylphenyl.
OTf refers to —O—C(CF$_3$)$_3$.
4NO$_2$-TPPOH refers to 4-nitro-2,3,5,6-tetraphenylphenol.

Example 1: Synthesis of Compound 2. A solution of TBS-Bitet-2-OH (115 mg) in 2 mL benzene was added dropwise to a solution of W(N-2,6-Cl$_2$C$_6$H$_3$)(CHCMe$_3$)—(NC$_4$(CH$_3$)$_2$H$_2$)$_2$ (135 mg) in benzene (2 mL). The reaction mixture was stirred at room temperature for 4 hours, and the volatile materials were removed under vacuum. The residue was dissolved in DME (1,2-dimethoxyethane) (2 mL) and a solution of 1-methoxy-2-vinylbenzene (54.5 mg) in DME (2 mL) was added in one portion and continued the stirring for further 4 hours. After that the reaction mixture was concentrated in vacuo to provide a deep-red oil from which the expected product was crystallized by n-pentane (91 mg). $^1$H-NMR (200 MHz, C$_6$D$_6$): δ−0.25 (s, 3H), 0.24 (s, 3H), 0.88 (s, 9H), 1.31-2.49 (m, 20H), 2.99-3.31 (m, 4H), 3.67 (s, 3H), 6.09-6.29 (m, 4H), 6.48 (t, J=8.2 Hz, 1H), 6.60-6.73 (m, 2H), 6.78-6.91 (m, 3H), 7.28 (s, 1H), 11.27 (s, 1H).

Example 2: Synthesis of Compound 3. A solution of W(N-2,6-Cl$_2$C$_6$H$_3$)(CHCMe$_3$)-(NC$_4$(CH$_3$)$_2$H$_2$)$_2$ (100 mg) in benzene (2 mL) was added to a solution of 4Br-TPPOH (79 mg) in benzene (2 mL). The reaction mixture was stirred at room temperature for 4 hours and the volatile materials were removed under vacuum. The residue was dissolved in 2 mL DME and a solution of 1-methoxy-2-vinylbenzene (45 mg) in DME (2 mL) was added in one portion and continued the stirring for further 4 hours. After that the reaction mixture was concentrated in vacuo to provide a red oil from which the expected product was crystallized by n-pentane (112 mg). $^1$H-NMR (200 MHz, C$_6$D$_6$): δ 1.87 (s, 6H), 3.21 (s, 3H), 5.88 (s, 2H), 6.15-6.30 (m, 2H), 6.42-6.61 (m, 2H), 6.71-7.09 (m, 20H), 11.19 (s, 3H).

Example 3: Synthesis of Compound 17. A solution of TBS-Bitet-2-OH (86 mg) in 2 mL benzene was added dropwise to a solution of W(N-2,6-Cl$_2$C$_6$H$_3$)(CHCMe$_3$)—(NC$_4$(CH$_3$)$_2$H$_2$)$_2$ (100 mg) in benzene (2 mL). The reaction mixture was stirred at room temperature for 4 hours and the volatile materials were removed under vacuum. The residue was dissolved in DME (2 mL) and a solution of 1-(methoxymethyl)-2-vinylbenzene (45 mg) in DME (2 mL) was added in one portion and continued the stirring for further 4 hours. After that the reaction mixture was concentrated in vacuo to provide a deep-red oil from which the expected product was crystallized by n-pentane (12 mg). $^1$H-NMR (200 MHz, C$_6$D$_6$): δ −0.12 (s, 3H), 0.21 (s, 3H), 0.79 (s, 9H), 1.16-1.64 (m, 10H), 1.85-2.55 (m, 14H), 3.19 (s, 3H), 5.99-6.33 (m, 3H), 6.44-6.83 (m, 5H), 7.18-7.35 (m, 3H), 11.58 (s, 1H).

Example 4: Synthesis of Compound 20. A solution of TBS-Bitet-2-OH (86 mg) in 2 mL benzene was added dropwise to a solution of W(N-2,6-Cl$_2$C$_6$H$_3$)(CHCMe$_3$)—(NC$_4$(CH$_3$)$_2$H$_2$)$_2$ (100 mg) in benzene (2 mL). The reaction mixture was stirred at room temperature for 4 hours and the volatile materials were removed under vacuum. The residue was dissolved in DME (2 mL) and a solution of 1-(dimethylamino)-2-vinylbenzene (45 mg) in DME (2 mL) was added in one portion and continued the stirring for further 4 hours. After that the reaction mixture was concentrated in vacuo to provide a deep-red oil from which the expected product was crystallized by n-pentane (58 mg). $^1$H-NMR (200 MHz, C$_6$D$_6$): δ −0.14 (s, 3H), 0.22 (s, 3H), 0.59 (s, 9H), 0.81 (s, 6H), 1.20-1.56 (m, 10H), 2.01-2.59 (m, 6H), 2.98 (s, 6H), 6.01-6.29 (m, 4H), 6.55 (t, J=8.1 Hz, 1H), 6.65-7.11 (m, 4H), 7.29 (s, 2H), 11.26 (s, 1H).

Example 5: Synthesis of Compound 16. A solution of TBS-Bitet-2-OH (86 mg) in 2 mL benzene was added dropwise to a solution of W(N-2,6-Cl$_2$C$_6$H$_3$)(CHCMe$_3$)—(NC$_4$(CH$_3$)$_2$H$_2$)$_2$ (100 mg) in benzene (2 mL). The reaction mixture was stirred at room temperature for 4 hours and the volatile materials were removed under vacuum. The residue was dissolved in DME (2 mL) and a solution of 1-(isopropoxy)-2-vinylbenzene (49 mg) in DME (2 mL) was added in one portion and continued the stirring for further 4 hours. After that the reaction mixture was concentrated in vacuo to provide a deep-red oil from which the expected product was crystallized by n-pentane (45 mg). $^1$H-NMR (200 MHz, C$_6$D$_6$): δ −0.10 (s, 3H), 0.01 (s, 9H), 0.38 (s, 3H), 0.85 (s, 6H), 1.00-1.60 (m, 16H), 1.90-2.60 (m, 6H), 4.93 (m, 1H), 6.04-6.24 (m, 3H), 6.44-6.65 (m, 2H), 6.70-6.81 (m, 3H), 6.95 (t, J=7.3 Hz, 1H), 7.22-7.26 (m, 2H), 11.44 (s, 1H).

Example 6: Synthesis of Compound 25. A solution of MeO-Bitet-2-OH (87 mg) in 2 mL benzene was added dropwise to a solution of Mo(N-2,6-(CH$_3$)$_2$C$_6$H$_3$)—(CHCMe$_2$Ph)(NC$_4$(CH$_3$)$_2$H$_2$)$_2$ (100 mg) in benzene (2 mL). The reaction mixture was stirred at room temperature for 4 hours and the volatile materials were removed under vacuum. The residue was dissolved in DME (2 mL) and a solution of 1-methoxy-2-vinylbenzene (50 mg) in DME (2 mL) was added in one portion and continued the stirring for further 4 hours. After that the reaction mixture was concentrated in vacuo to provide a deep-red oil from which the expected product was crystallized by n-pentane (45 mg). $^1$H-NMR (200 MHz, C$_6$D$_6$) (mixture of diastereomers): δ 1.25-1.53 (m, 22H), 1.88-2.56 (m, 30H), 3.41$^x$ (s, 2.5H), 3.45 (s, 3H), 3.51$^x$ (s, 2.5H), 3.53 (s, 3H), 6.13 (s, 3.7H), 6.30-7.30 (m, 17H), 12.86 (s, 1H), 13.05$^x$ (s, 0.85H).

Example 7: Synthesis of Compound 26. A solution of MeO-Bitet-2-OH (79 mg) in 2 mL benzene was added dropwise to a solution of Mo(N-2,6-i-Pr$_2$C$_6$H$_3$)(CHCMe$_2$Ph)-(NC$_4$(CH$_3$)$_2$H$_2$)$_2$ (100 mg) in benzene (2 mL). The reaction mixture was stirred at room temperature for 4 hours and the volatile materials were removed under vacuum. The residue was dissolved in DME (2 mL) and a solution of 1-methoxy-2-vinylbenzene (45 mg) in DME (2 mL) was added in one portion and continued the stirring for further 4 hours. After that the reaction mixture was concentrated in vacuo to provide a deep-red oil from which the expected product was crystallized by n-pentane (40 mg). $^1$H-NMR (200 MHz, C$_6$D$_6$): δ 1.12 (d, J=6.8 Hz, 6H), 1.19 (d, J=6.8 Hz, 6H), 1.28-1.54 (m, 14H), 2.00-2.50 (m, 10H), 3.42 (s, 3H), 3.51 (m, 5H), 6.11 (s, 2H), 6.27 (d, J=7.3 Hz, 1H), 6.51 (d, J=7.9 Hz, 1H), 6.66-6.86 (m, 3H), 6.89-7.09 (m, 4H), 12.94 (s, 1H).

Example 8: Synthesis of Compound 33. A solution of triphenylsilanol (355 mg) in 3 mL benzene was added dropwise to a solution of Mo(N-2,6-i-Pr$_2$C$_6$H$_3$)(CHCMe$_2$Ph)-(NC$_4$(CH$_3$)$_2$H$_2$)$_2$ (328 mg) in benzene (3 mL). The reaction mixture was stirred at room temperature for 4 hours and the volatile materials were removed under vacuum. The residue was dissolved in DME (10 mL) and a solution of 1-methoxy-2-vinylbenzene (164 mg) in DME (5 mL) was added in one portion and continued the stirring for further 4 hours. After that the reaction mixture was concentrated in vacuo to provide a deep-red oil from which the expected product was crystallized by n-pentane (228 mg). $^1$H-NMR (300 MHz, C$_6$D$_6$): δ 1.02 (s, 6H), 1.04 (s, 6H), 3.08 (s, 3H), 4.09 (m, 2H), 6.04 (d, J=7.8 Hz, 1H), 6.42 (d, J=7.9 Hz, 1H), 6.57 (t, J=7.5 Hz, 1H), 6.87 (t, J=7.5 Hz, 1H), 6.95-7.12 (m, 21H), 7.65-7.72 (m, 12H), 12.35 (s, 1H).

Example 9: Synthesis of Compound 34. Lithium salt of triphenylsilanol (676 mg) was added to the solution of W(N-2,6-i-Pr$_2$C$_6$H$_3$)(CHCMe$_2$Ph)(OTf)$_2$DME (1.00 g) in toluene (10 mL) at −30° C., and the suspension was stirred at room temperature overnight. After completion of the reaction, it was filtered through a Celite pad and the filtrate was concentrated to yield a brown solid. The solid precipitate was dissolved in DME (5 mL), and a solution of 1-methoxy-2-vinylbenzene (306 mg) in DME (5 mL) was added in one portion and continued the stirring for further 4 hours. After that the reaction mixture was concentrated in vacuo to provide a deep-red oil from which the product was crystallized in n-pentane (464 mg). 1H-NMR (300 MHz, C$_6$D$_6$): δ 1.17 (d, J=6.8 Hz, 6H), 1.26 (d, J=6.8 Hz, 6H), 1.70 (s, 6H), 3.86 (m, 2H), 5.54 (d, J=7.8 Hz, 1H), 5.86 (s, 2H), 6.16-6.22 (m, 1H), 6.60-7.10 (m, 24H), 7.55 (m, 1H), 11.52 (s, 1H).

Example 10: Synthesis of Compound 35. A solution of W(N-2,6-Cl$_2$C$_6$H$_3$)(CHCMe$_3$)—(NC$_4$(CH$_3$)$_2$H$_2$)$_2$ (200 mg) in benzene (3 mL) was added to a solution of 4Br-TPPOH (166 mg) in benzene (3 mL). The reaction mixture was stirred at room temperature for 4 hours, and the volatile materials were removed under vacuum. The residue was dissolved in 5 mL DME, and a solution of 2-vinylpyridine (105 mg) in DME (2 mL) was added in one portion and continued the stirring for an additional 4 hours. After that, the reaction mixture was concentrated in vacuo to provide a red oil from which the product was crystallized by n-pentane (171 mg). 1H-NMR (300 MHz, $C_6D_6$): δ 1.96 (s, 6H), 5.53 (d, J=7.8 Hz), 5.92 (s, 2H), 6.02 (m, 1H), 6.16 (t, J=8.0 Hz, 1H), 6.55 (m, 1H), 6.60-7.05 (m, 20H), 7.60 (m, 1H), 8.06 (s, 1H), 8.48 (m, 1H), 10.53 (s, 1H).

Example 11: Synthesis of Compound 36. A solution of Mo(N-2,6-i-$Pr_2C_6H_3$)—(CHCMe$_2$Ph)(NC$_4$(CH$_3$)$_2$H$_2$)$_2$ (200 mg) in benzene (3 mL) was added to a solution of 4Br-TPPOH (161 mg) in benzene (3 mL). The reaction mixture was stirred at room temperature for 4 hours and the volatile materials were removed under vacuum. The residue was dissolved in 5 mL DME and a solution of 2-vinylpyridine (72 mg) in DME (2 mL) was added in one portion, and the stirring was continued for another 4 hours. After that, the reaction mixture was concentrated in vacuo to provide a brown oil from which the product was crystallized by n-pentane (215 mg). 1H-NMR (300 MHz, $C_6D_6$): δ 1.17 (d, J=6.8 Hz, 6H), 1.27 (d, J=6.8 Hz, 6H), 1.70 (s, 6H), 3.82-3.88 (m, 2H), 5.54 (d, J=7.8 Hz, 1H), 5.89 (s, 2H), 6.16-6.23 (m, 1H), 6.60-7.10 (m, 24H), 7.53-7.57 (m, 1H), 11.52 (s, 1H).

Example 12: Synthesis of Compound 37. Compound 4 (100 mg) was dissolved in benzene (1 mL) and the solution of 1,1,1,3,3,3-hexafluoro-2-methylpropan-2-ol (18.9 mg) in benzene (1 mL) was added dropwise to the solution at room temperature. After the addition was completed, the reaction mixture was stirred for 4 hours at the same temperature, then it was concentrated in vacuo to provide a brown oil from which the product was crystallized by n-pentane (53 mg). 1H-NMR (300 MHz, C6D6): δ 0.99 (s, 3H), 1.28 (d, J=6.8 Hz, 6H), 1.33 (d, J=6.8 Hz, 6H), 3.20 (s, 3H), 3.84 (m, 2H), 6.18-7.10 (m, 24H), 7.22-7.80 (m, 3H), 11.99 (s, 1H).

Example 13: Synthesis Compound 40. To a homogenous solution of Mo(N-2,6-i-$Pr_2C_6H_3$)(CHCMe$_2$Ph)(NC$_4$(CH$_3$)$_2$H$_2$)(4Br-TPPO) (972 mg), which was readily prepared in a stoichiometric reaction of Mo(N-2,6-i-$Pr_2C_6H_3$)(CHCMe$_2$Ph)-(NC$_4$(CH$_3$)$_2$H$_2$)$_2$ precursor and 4Br-TPPOH in anhydrous benzene at ambient temperature, in a 1:1 mixture of anhydrous benzene and DME (10 mL), 2-vinyloxitetrahydropyrane (138 μL) was added, and the reaction mixture was stirred for an additional 24 hours at ambient temperature. Then the volatiles were removed under reduced pressure, and the remaining powdery residue was recrystallized from hot benzene to obtain brick red micro-crystals (420 mg). 1H-NMR (300 MHz, C6D6): δ 0.73 (m, J=11 Hz, 2H), 1.07 (q, J=13 Hz, 1H), 1.27 (m, 1H), 1.25 (d, J=7 Hz 6H), 1.28 (d, J=7 Hz 6H), 1.38 (q, 1H), 1.51 (s, 3H), 1.78 (d, J=13 Hz, 1H), 2.20 (s, 3H), 2.38 (t, J=12 Hz, 1H), 3.69 (d, J=12 Hz, 1H), 4.21 (sept. J=7 Hz, 2H), 5.00 (dd, J=10, 2 Hz), 5.93 (s, 1H), 6.21 (s, 1H), 6.60-7.90 (m, 23H), 11.05 (s, 1H) ppm.

Example 14: Synthesis Compound 41. The potassium salt of 2-ethoxyindole (0.79 g) was added to the solution of Mo(N-2,6-i-$Pr_2C_6H_3$)(CHCMe2Ph)(OTf)$_2$DME (1.50 g) in toluene (15 mL) at −30° C., and the suspension was stirred at room temperature overnight. After completion of the reaction, it was filtered through a Celite pad and the filtrate was concentrated to yield an orange solid. The solid precipitate (150 mg) was dissolved in benzene (3 mL) and the solution of 4Br-TPPOH (104 mg) in benzene (3 mL) was added to the reaction mixture and it was stirred at room temperature for 4 hours, and the volatile materials were removed under vacuum. The residue was dissolved in 5 mL DME and a solution of 2-vinylbenzene (33 mg) in DME (1 mL) was added in one portion, and the stirring was continued for an additional 4 hours. After that, the reaction mixture was concentrated in vacuo to provide a red oil from which the product was crystallized by n-pentane (145 mg). 1H-NMR (300 MHz, C6D6): δ 0.86 (t, J=7.1 Hz, 3H), 0.99 (d, J=6.7 Hz, 6H), 1.25 (d, J=6.8 Hz, 6H), 3.20-3.80 (m, 7H), 5.28 (s, 1H), 6.30-7.40 (m, 31H), 12.55 (s, 1H).

Example 15: Synthesis Compound 50. A solution of Mo(N-2,6-i-$Pr_2C_6H_3$) (CHCMe$_2$Ph)(NC$_4$(CH$_3$)$_2$H$_2$)$_2$ (200 mg) in benzene (3 mL) was added to a solution of 4Br-TPPOH (161 mg) in benzene (3 mL). The reaction mixture was stirred at room temperature for 4 hours and the volatile materials were removed under vacuum. The residue was dissolved in 5 mL DME and a solution of acetic acid ethenyl ester (58 mg) in DME (2 mL) was added in one portion, and the stirring was continued for another 4 hours. After that, the reaction mixture was concentrated in vacuo to provide a brown oil from which the product was crystallized by n-pentane (192 mg). 1H-NMR (300 MHz, C6D6): δ 1.08 (d, J=6.7 Hz, 6H), 1.19 (d, J=6.6 Hz, 6H), 1.73 (s, 6H), 1.79 (s, 3H), 3.70 (m, 2H), 5.95 (s, 2H), 6.70-7.50 (m, 23H), 10.61 (s, 1H).

Example 16: Synthesis Compound 55. A solution of Mo(N-2,6-i-$Pr_2C_6H_3$) (CHCMe$_2$Ph)(NC$_4$(CH$_3$)$_2$H$_2$)$_2$ (200 mg) in benzene (3 mL) was added to a solution of 4Br-TPPOH (161 mg) in benzene (3 mL). The reaction mixture was stirred at room temperature for 4 hours and the volatile materials were removed under vacuum. The residue was dissolved in 5 mL DME and a solution of 2-methoxy-4-nitro-1-vinylbenzene (96 mg) in DME (2 mL) was added in one portion, and the stirring was continued for another 4 hours. After that, the reaction mixture was concentrated in vacuo to provide a brown oil from which the product was crystallized by n-pentane (293 mg). 1H-NMR (300 MHz, C6D6): δ 1.15 (d, J=6.8 Hz, 6H), 1.24 (d, J=6.8 Hz, 6H), 1.43 (s, 6H), 3.27 (s, 3H), 3.65 (m, 2H), 5.74 (d, J=8.4 Hz, 1H), 5.86 (s, 2H), 6.50-7.20 (m, 23H), 7.53 (m, 1H), 7.66 (dd, $J_1$=8.4 Hz, $J_2$=1.9 Hz, 1H), 12.05 (s, 1H).

Example 17: Synthesis Compound 57. A solution of Mo(N-2,6-i-$Pr_2C_6H_3$) (CHCMe$_2$Ph)(NC$_4$(CH$_3$)$_2$H$_2$)$_2$ (125 mg) in benzene (2 mL) was added to a solution of 4NO$_2$-TPPOH (98 mg) in benzene (2 mL). The reaction mixture was stirred at room temperature for 4 hours and the volatile materials were removed under vacuum. The residue was dissolved in 2 mL DME and a solution of 2-methoxy-1-vinylbenzene (18 mg) in DME (1 mL) was added in one portion, and the stirring was continued for another 4 hours. After that, the reaction mixture was concentrated in vacuo to provide a brown oil from which the product was crystallized by diethyl ether (81 mg). 1H-NMR (300 MHz, C6D6): δ 1.18 (d, J=6.8 Hz, 6H), 1.29 (d, J=6.8 Hz, 6H), 1.51 (s, 6H), 3.37 (s, 3H), 3.85 (m, 2H), 5.79 (s, 1H), 5.92 (s, 1H), 6.04 (m, 1H), 6.43 (m, 1H), 6.60-7.40 (m, 25H), 12.42 (s, 1H).

The other compounds set forth in Table 2, above, were also synthesized by analogous methods. Each of the compounds was analyzed by 1H NMR. Table 3, below, shows the chemical shift for the alkylidene hydrogen (in ppm).

TABLE 3

| Compound No. | δ for Alkylidene Peak (ppm) |
|---|---|
| 1 | 12.43 |
| 2 | 11.28 |
| 3 | 11.19 |
| 4 | 12.44 |

TABLE 3-continued

| Compound No. | δ for Alkylidene Peak (ppm) |
|---|---|
| 5 | 11.12 |
| 6 | 10.99 |
| 7 | 12.01, 11.96 |
| 8 | 11.18 |
| 9 | 11.25 |
| 10 | 10.37, 9.86 |
| 11 | 11.23 |
| 12 | 11.29 |
| 13 | 11.14 |
| 14 | 11.93 |
| 15 | 11.25 |
| 16 | 11.44 |
| 17 | 11.58 |
| 18 | 12.66 |
| 19 | 12.80 |
| 20 | 11.26 |
| 21 | 12.51 |
| 22 | 11.77, 11.48 |
| 23 | 12.98 |
| 24 | 13.23, 13.06 |
| 25 | 13.05, 12.86 |
| 26 | 12.94 |
| 27 | 11.12 |
| 28 | 11.02 |
| 29 | 11.15 |
| 30 | 11.19 |
| 31 | 11.13 |
| 32 | 11.84 |
| 33 | 12.35 |
| 34 | 10.54 |
| 35 | 10.53 |
| 36 | 11.52 |
| 37 | 11.99 |
| 38 | 12.11 |
| 39 | 11.98 |
| 40 | 11.05 |
| 41 | 12.55 |
| 42 | 10.16 |
| 43 | 10.30 |
| 44 | 10.35 |
| 45 | 12.12 |
| 46 | 11.05 |
| 47 | 13.33 |
| 48 | 12.29 |
| 49 | 11.18 |
| 50 | 10.61 |
| 51 | 10.92 |
| 52 | 10.82 |
| 53 | 11.87 |
| 54 | 10.93 |
| 55 | 12.05 |
| 56 | 10.86 |
| 57 | 12.42 |
| 58 | 11.18 |
| 59 | 11.02 |
| 60 | 11.05 |
| 61 | 10.41 |
| 62 | 9.89 |
| 63 | 12.23 |
| 64 | 10.95 |

Experimental Details on Metathesis Reaction with Compounds Disclosed Herein

The compounds disclosed above were screened for catalytic activity in certain metathesis reactions. The results are indicated below.

General Procedures for Screening Reactions

For the reaction of oct-1-ene, methyl 9-decenoate, and allylbenzene. In a nitrogen-filled glovebox, a glass vial was charged with the olefin substrate (2.23-2.54 mmol), then a solution of catalyst in benzene (0.025-0.1 M) was added to the vial in one portion and the mixture was allowed to stir at 22° C. for 15 hours. After that, an aliquot of the reaction was quenched by diethyl ether (100 µL) and the conversion, E/Z selectivity were monitored by GC-MS.

For self-metathesis of diethyl diallylmalonate. In a nitrogen-filled glovebox, a glass vial was charged with diethyl diallylmalonate (0.832 mmol) and 1 mL of toluene. A solution of catalyst in benzene (0.025-0.1 M) was added to the vial in one portion and the mixture was allowed to stir at 22° C. for 15 hours. After that, an aliquot of the reaction was quenched by diethyl ether (100 µL) and the conversion was monitored by GC-MS.

GC-MS analytical method for oct-1-ene, methyl 9-decenoate, and allylbenzene. The GC analyses were run using a flame ionization detector (FID). Column: ZB-35HT Inferno (35% Phenyl, 65% Dimethylpolysiloxane) from Phenomenex; 30 m×0.25 mm (i.d.)×0.25 mm film thickness. GC and column conditions: injector temperature of 370° C.; detector temperature 240° C.; oven temperature, starting temperature 50° C., hold time 5 minutes, ramp rate 25° C./min to 340° C., hold time 12 minutes; carrier gas nitrogen.

GC-MS analytical method for diethyl diallylmalonate. The GC analyses were run using a flame ionization detector (FID). Column: ZB-1HT Inferno (100% Dimethylpolysiloxane) from Phenomenex; 30 m×0.25 mm (i.d.)×0.25 mm film thickness. GC and column conditions: injector temperature 370° C.; detector temperature 240° C.; oven temperature, starting temperature 50° C., hold time 5 minutes, ramp rate 25° C./min to 340° C., hold time 12 minutes; carrier gas nitrogen.

Compound Activity and Comparison with Known Complexes

Nine complexes, here designated Compounds A to I (below):

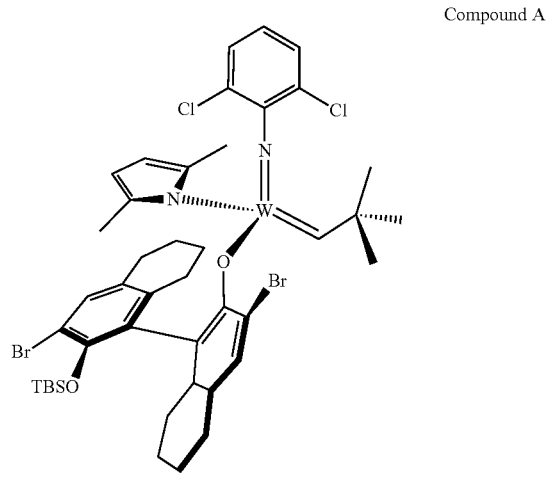

Compound A

Compound B
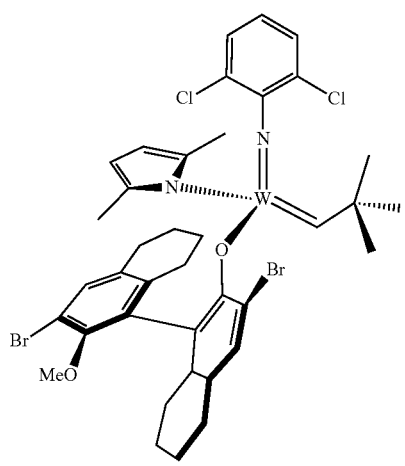
Compound C
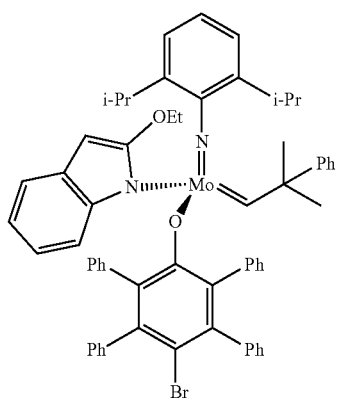
Compound D
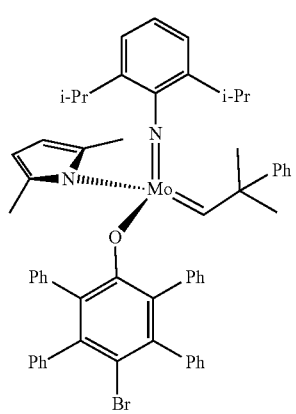
Compound E
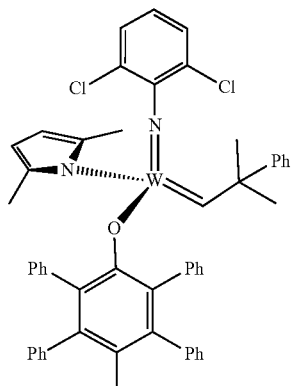
Compound F
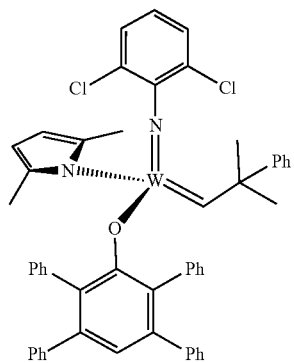
Compound G
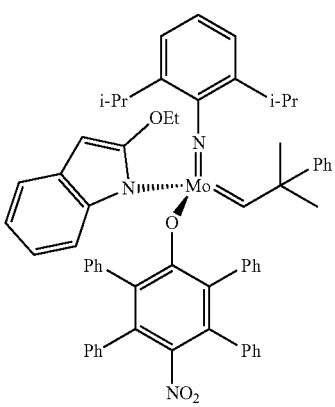
Compound H
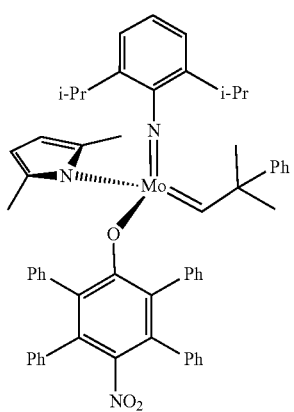

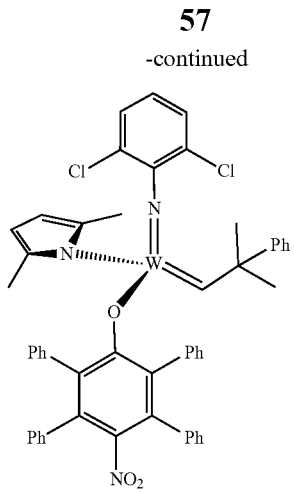

Compound I were used as comparative examples in the experiments shown below. Thus, in any of the below experimental examples, reference to a compound by letter, e.g., "A", refers to Compound A, above, and so forth for Compounds B through I.

Homo-Metathesis of oct-1-ene.

Comparative compounds A and B were compared with compounds of the present disclosure, Compounds 15, 17 and 22, in the homo-metathesis of oct-1-ene. Table 4 (below) shows the Conversion % at various catalyst loadings (in molar ppm). Conversion refers to the percent of the substrate (i.e., oct-1-ene) converted to the product (i.e., E/Z-7-heptene). Conversion %=100−{[(final moles of reagent)×100]/[initial moles of reagent]}. The catalyst loadings ("Loading") are calculated relative to the initial concentration of the metathesis substrate.

TABLE 4

| Compound | Loading (mol ppm) | Conversion % |
| --- | --- | --- |
| A | 50 | 59 |
| B | 50 | 49 |
| 15 | 50 | 62 |
| 17 | 50 | 69 |
| 22 | 50 | 83 |

Homo-Metathesis of Allykbenzene.

Table 5 (below) shows the comparison of catalytic activity for Compound A and for Compounds 2, 5, 9, and 11 of the present disclosure in the homo-metathesis of allylbenzene. The loading and the conversion percentage are calculated as above. The ratio of E isomers formed relative to Z isomers formed is also determined.

TABLE 5

| Compound | Loading (mol ppm) | Conversion % | E/Z ratio |
| --- | --- | --- | --- |
| A | 100 | 95 | 37/63 |
| 2 | 100 | 90 | 12/88 |
| 5 | 100 | 92 | 19/81 |
| 9 | 100 | 91 | 19/81 |
| 11 | 100 | 92 | 17/83 |
| A | 50 | 91 | 40/60 |
| 2 | 50 | 63 | 5/95 |
| 5 | 50 | 52 | 5/95 |
| 9 | 50 | 63 | 6/94 |
| 11 | 50 | 60 | 5/95 |

Ring-Closing Metathesis of Diethyl Diallylmalonate.

Table 6 shows the catalytic activity for certain compounds disclosed herein in the ring-closing metathesis of diethyl diallylmalonate. Loading and conversion percentage have the same meanings as above.

TABLE 6

| Compound | Loading (mol ppm) | Conversion % |
| --- | --- | --- |
| 2 | 200 | 93 |
| 3 | 200 | 65 |
| 5 | 200 | 97 |
| 6 | 200 | 72 |
| 7 | 200 | 63 |
| 8 | 200 | 92 |
| 9 | 200 | 96 |
| 11 | 200 | 95 |
| 12 | 200 | 91 |
| 13 | 200 | 87 |
| 15 | 200 | 96 |
| 16 | 200 | 75 |
| 17 | 200 | 79 |
| 22 | 200 | 99 |

Cross-Metathesis of Unsaturated Triglyceride with Ethylene.

Table 7 shows the comparison of catalytic activity of Compounds 3 and 4 of the present disclosure with that of Compounds D and E (shown below) for the cross-metathesis of food-grade canola oil (triglyceride ("TG")) with ethylene to yield. The canola oil was pre-treated with 6.5 mol % triethylaluminum at 50° C. at 10 atm for 18 hours. The product mixture was analyzed by gas chromatography with a flame ionization detector (GC-FID) to determine the conversion percentage, the product being transesterified with methanol prior to GC-FID analysis. The conversion percentage was calculated as follows: Conversion %=100−[(final moles of TG)×100/(initial moles of TG)]. Selectivity was also determined, which is defined as follows: Selectivity=(moles of methyl 9-decenoate)×100/(total moles of all methyl esters in the product mixture except methyl 9-decenoate precursor esters and the saturated esters coming from canola oil). The yield of methyl 9-decenoate (9DAME) was also calculated, which is defined as: Yield=(moles of 9DAME)×100/(initial moles of 9DAME precursor chains in canola oil). In Table 7, the catalyst loadings are given in terms of ppm weight (relative to metathesis substrate). The catalytic activity of compounds disclosed herein is compared to Compounds C, D, E, and F.

TABLE 7

| Compound | Loading (wt ppm) | Conversion % | Selectivity | Yield |
| --- | --- | --- | --- | --- |
| D | 1000 | 17 | 9 | 9 |
| 4 | 1000 | 93 | 50 | 45 |
| 60 | 1000 | 97 | 47 | 46 |
| 36 | 1000 | 90 | 53 | 45 |
| 50 | 1000 | 49 | 59 | 33 |
| C | 1000 | 46 | 63 | 24 |
| 41 | 1000 | 75 | 67 | 41 |
| E | 250 | 40 | 56 | 23 |
| 3 | 250 | 56 | 67 | 38 |
| 35 | 1000 | 80 | 56 | 45 |
| 40 | 1000 | 97 | 47 | 46 |
| 40 | 25 | 27 | 55 | 16 |
| F | 1000 | 58 | 67 | 39 |
| 59 | 1000 | 91 | 73 | 54 |

Homo-Metathesis of Methyl 9-Decenoate.

Table 8 shows the catalytic activity for certain compounds disclosed herein in the self-metathesis of methyl 9-decenoate. Loading and conversion percentage have the same meanings as in Table 6.

TABLE 8

| Compound | Loading (mol ppm) | Conversion % |
|---|---|---|
| 35 | 33 | 67 |
| 36 | 33 | 89 |
| 40 | 33 | 92 |

Thermal Stability of Catalysts—Decomposition Temperature.

Table 9 shows the thermal stability of comparative Compounds G, H, and I in comparison to compounds of the present disclosure. Thermal stability was determined by dissolving 10 mg of the test samples in 1 mL of 1,1,2,2-tetrachloroethane-$d_2$; the samples were then heated to 60° C., 90° C., and 120° C. and held at that temperature for 1 hour, after which the samples were cooled to room temperature and the $^1$H-NMR spectrum was recorded for each. The decomposition temperature refers to the temperature at which decomposition of the catalyst was first observed, as measured by a decrease in the intensity of the peak in the $^1$H NMR spectrum corresponding to the alkylidene proton.

TABLE 9

| Compound | Decomposition Temp. (° C.) |
|---|---|
| G | 90 |
| 41 | 120 |
| H | 60 |
| 56 | 120 |
| I | 60 |
| 58 | 120 |

Thermal Stability of Catalysts—Thermal Stability Over Time

Table 10 shows the air stability over time for comparative Compounds A, D, and E in comparison to compounds of the present disclosure. For this experiment, a 10-mg sample of the catalyst, in solid crystalline form, was exposed to atmospheric conditions for 30 minutes, 60 minutes, and 24 hours. After exposing the sample to atmospheric conditions, the sample was dissolved in 1 mL of benzene-$d_6$ and the $^1$H NMR spectrum was recorded. The percentage decomposition refers to the percentage reduction in the intensity of peak in the $^1$H NMR spectrum corresponding to the alkylidene proton in comparison to the intensity of the same peak for a sample of the same compound that was kept in a glovebox and not exposed to atmospheric conditions. The term "decomposed" refers to 100% decomposition.

TABLE 10

| Compound | Decomposition after 30 minutes | Decomposition after 60 minutes | Decomposition after 24 hours |
|---|---|---|---|
| D | 65% | decomposed | decomposed |
| 4 | 0% | 0% | 5% |
| 61 | 45% | 85% | decomposed |
| E | 85% | decomposed | decomposed |
| 3 | 15% | 40% | decomposed |
| 62 | 30% | 65% | decomposed |
| A | 90% | decomposed | decomposed |
| 2 | 25% | 50% | decomposed |

The invention claimed is:

1. A compound of Formula (II)

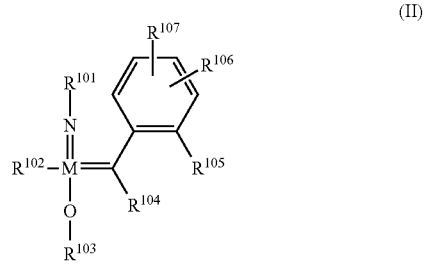

wherein:

M is a molybdenum atom or a tungsten atom;

$R^{101}$ is phenyl, alkyl, or cycloalkyl, each of which is optionally substituted;

$R^{102}$ is pyrrolyl or indolyl, each of which is optionally substituted;

$R^{103}$ is phenyl, optionally substituted;

$R^{104}$ is a hydrogen atom;

$R^{105}$ is —O—($C_{1-6}$ alkyl) or —$CH_2$—O—($C_{1-6}$ alkyl); and $R^{106}$ and $R^{107}$ are independently a hydrogen atom, $C_{1-6}$ alkyl, $C_{1-6}$ alkoxy, or a halogen atom.

2. The compound of claim 1, wherein $R^{101}$ is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

3. The compound of claim 1, wherein $R^{102}$ is pyrrol-1-yl, 2,5-dimethylpyrrol-1-yl, 2,5-diphenylpyrrol-1-yl, or indol-1-yl.

4. The compound of claim 1, wherein $R^{105}$ is methyloxy, ethyloxy, or isopropyloxy.

5. The compound of claim 1, wherein $R^{106}$ and $R^{107}$ are independently a hydrogen atom, methyl, a halogen atom, or methyloxy.

6. A method for carrying out a metathesis reaction, the method comprising:

providing a first compound having one or more carbon-carbon double bonds; and reacting the first compound via a metathesis reaction in the presence of a compound of claim 1.

7. The method of claim 6, wherein the first compound has two or more carbon-carbon double bonds.

8. The method of claim 7, wherein the metathesis reaction is a ring-closing metathesis reaction between two of the two or more carbon-carbon double bonds of the first compound.

9. A method of carrying out a metathesis reaction, the method comprising:

providing a first compound having one or more carbon-carbon double bonds and a second compound having one or more carbon-carbon double bonds; and reacting the first compound and the second compound via a metathesis reaction in the presence of a compound of Formula (II)

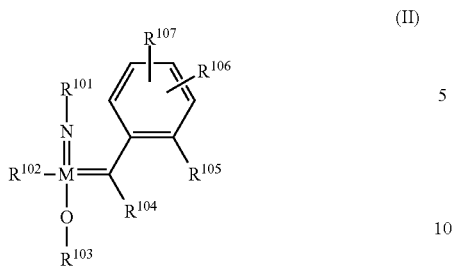

(II)

wherein:

M is a molybdenum atom or a tungsten atom;

$R^{101}$ is aryl, heteroaryl, alkyl, or cycloalkyl, each of which is optionally substituted;

$R^{102}$ is pyrrolyl or indolyl, each of which is optionally substituted;

$R^{103}$ is $C_{1-6}$, alkyl, $C_{1-6}$ heteroalkyl, aryl, or heteroaryl, optionally substituted;

$R^{104}$ is a hydrogen atom;

$R^{105}$ is —O—($C_{1-6}$ alkyl) or —$CH_2$—O—($C_{1-6}$ alkyl); and $R^{106}$ and $R^{107}$ are independently a hydrogen atom, $C_{1-6}$ alkyl, $C_{1-6}$ alkoxy, or a halogen atom, wherein the first compound and the second compound are the same compound.

10. The compound of claim 1, comprising a neutral ligand.

\* \* \* \* \*